(12) United States Patent
Frey et al.

(10) Patent No.: US 11,145,826 B2
(45) Date of Patent: Oct. 12, 2021

(54) COMPOUND FOR ELECTRONIC DEVICE AND ELECTRONIC DEVICE AND DISPLAY DEVICE

(71) Applicants: Novaled GmbH, Dresden (DE); Samsung SDI Co., Ltd., Gyeonggi-do (KR)

(72) Inventors: Julien Frey, Dresden (DE); Domagoj Pavicic, Dresden (DE); Volodymyr Senkovskyy, Dresden (DE); Elena Galan, Dresden (DE); Hyungsun Kim, Gyeonggi-do (KR); Byungku Kim, Gyeonggi-do (KR)

(73) Assignees: Novaled GmbH, Dresden (DE); Samsung SDI Co., Ltd., Gyeonggi-do (KR)

( * ) Notice: Subject to any disclaimer, the term of this patent is extended or adjusted under 35 U.S.C. 154(b) by 371 days.

(21) Appl. No.: 16/344,426

(22) PCT Filed: Oct. 18, 2017

(86) PCT No.: PCT/EP2017/076578
§ 371 (c)(1),
(2) Date: Apr. 24, 2019

(87) PCT Pub. No.: WO2018/077689
PCT Pub. Date: May 3, 2018

(65) Prior Publication Data
US 2020/0058880 A1 Feb. 20, 2020

(30) Foreign Application Priority Data
Oct. 24, 2016 (EP) .................................. 16195345.0

(51) Int. Cl.
*C07D 219/02* (2006.01)
*H01L 51/00* (2006.01)
(Continued)

(52) U.S. Cl.
CPC ........ *H01L 51/0072* (2013.01); *C07D 219/02* (2013.01); *C07D 401/14* (2013.01);
(Continued)

(58) Field of Classification Search
None
See application file for complete search history.

(56) References Cited

FOREIGN PATENT DOCUMENTS

| WO | 2011/154131 A1 | 12/2011 |
| WO | 2013/079217 A1 | 6/2013 |

OTHER PUBLICATIONS

PCT International Search Report and Written Opinion for PCT Application No. PCT/EP2017/076578 dated Dec. 14, 2017 (8 pages).

*Primary Examiner* — Clinton A Brooks
(74) *Attorney, Agent, or Firm* — Eversheds Sutherland (US) LLP

(57) ABSTRACT

The present invention relates to a compound of an acridine derivate as well as of an organic semiconductor material an organic semiconductor layer, an electronic device comprising the acridine derivative, a device comprising an organic light-emitting diode comprising the acridine derivative, a display device thereof and a method of manufacturing the same. (I) wherein L is selected from phenylene, naphthylene and biphenylene; $R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; a, b, c, d and e are independently selected from 0 or 1 and $2 \leq a+b+c+d+e \leq 5$.

(Continued)

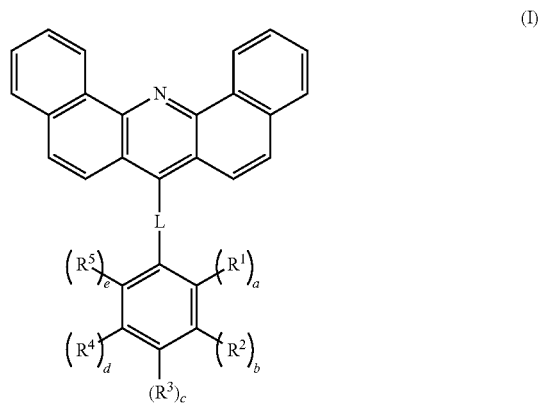
(I)
20 Claims, 2 Drawing Sheets
(51) Int. Cl.
 *C07D 401/14* (2006.01)
 *C09K 11/06* (2006.01)
(52) U.S. Cl.
 CPC .......... *C09K 11/06* (2013.01); *H01L 51/0052* (2013.01); *H01L 51/0058* (2013.01); *H01L 51/0067* (2013.01); *C09K 2211/1018* (2013.01)

COMPOUND FOR ELECTRONIC DEVICE AND ELECTRONIC DEVICE AND DISPLAY DEVICE

CROSS REFERENCE TO RELATED APPLICATIONS

This application is a U.S. national stage application of PCT/EP2017/076578, filed Oct. 18, 2017, which claims priority to European Application No. 16195345.0, filed Oct. 24, 2016. The contents of these applications are hereby incorporated by reference.

TECHNICAL FIELD

The present invention relates to a compound of an acridine derivate as well as of an organic semiconductor material, an organic semiconductor layer, an electronic device comprising the acridine derivative, a device comprising an organic light-emitting diode comprising the acridine derivative, a display device thereof and a method of manufacturing the same.

BACKGROUND ART

Organic light-emitting diodes OLEDs, which are self-emitting devices, have a wide viewing angle, excellent contrast, quick response, high brightness, excellent driving voltage characteristics, and color reproduction. A typical OLED includes an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

Particularly, development for an organic material being capable of increasing electron mobility and simultaneously increasing electrochemical stability is needed so that the organic light emitting diode may be applied to a large-size flat panel display.

WO2011154131A1 relates to an electronic device comprising at least one organic semiconducting material according to the following formula (A): wherein R1-4 are independently selected from H, halogen, CN, substituted or unsubstituted C1-C20-alkyl or heteroalkyl, C6-C20-aryl or C5-C20-heteroaryl, C1-C20-alkoxy or C6-C20-aryloxy, Ar is selected from substituted or unsubstituted C6-C20-aryl or C5-C20-heteroaryl, and R5 is selected from substituted or unsubstituted C6-C20-aryl or C5-C20-heteroaryl, H, F or formula (B).

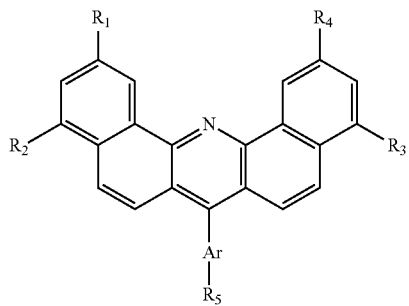

(A)

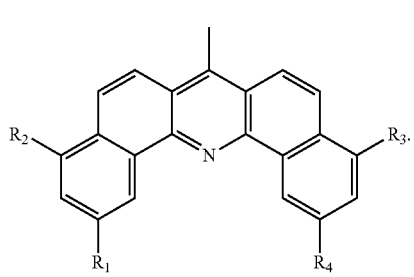

(B)

The glass transition temperature is low and operating voltage, cd/A efficiency and lifetime are poor of OLEDs comprising these materials.

In light of the prior art, there remains a need to improve performance of OLEDs and organic semiconductor materials, in particular achieve higher efficiency and/or longer lifetime through improving the characteristics of the compounds comprised therein.

DISCLOSURE

An aspect of the present invention provides a compound of formula (I):

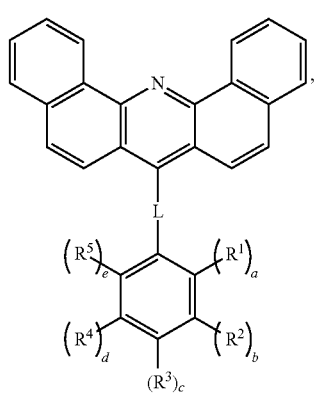

(I)

wherein

L is selected from phenylene, naphthylene and biphenylene;

$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, b, c, d and e are independently selected from 0 or 1 and $2 \leq a+b+c+d+e \leq 5$.

In the specification the wording "the substituents are selected from deuterium, $C_1$ to $C_{12}$ alkyl and $C_1$ to $C_{12}$ alkoxy" refers to $R^1$, $R^2$, $R^3$, $R^4$ and $R^5$, if not otherwise stated.

The compound represented by formula I, and a composition comprising the compound represented by formula I have strong electron transport characteristics to increase charge mobility and stability and thereby to improve luminance efficiency, voltage characteristics, and life-span characteristics. The composition may be used in an electron transport layer as well as an emission layer, and the compound represented by formula I may be used alone in the electron transport layer.

In the present specification, when a definition is not otherwise provided, "substituted" may refers to one substituted with a deuterium, $C_1$ to $C_{12}$ alkyl and $C_1$ to $C_{12}$ alkoxy.

In the present specification, when a definition is not otherwise provided, an "alkyl group" may refers to an aliphatic hydrocarbon group. The alkyl group may refer to "a saturated alkyl group" without any double bond or triple bond.

The alkyl group may be a $C_1$ to $C_{12}$ alkyl group. More specifically, the alkyl group may be a $C_1$ to $C_{10}$ alkyl group or a $C_1$ to $C_6$ alkyl group. For example, a $C_1$ to $C_4$ alkyl group includes 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification "aryl group" may refers to a group including at least one hydrocarbon aromatic moiety, and all the elements of the hydrocarbon aromatic moiety may have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like.

The aryl group may include a monocyclic, polycyclic or fused ring polycyclic (i.e., rings sharing adjacent pairs of carbon atoms) functional group.

In the present specification, the single bond refers to a direct bond.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

According to another embodiment $R^1$, $R^2$, $R^3$, $R^4$ and $R^5$ may be independently selected from unsubstituted or substituted $C_6$ to $C_{12}$ aryl and unsubstituted or substituted pyridyl; and the substituents are selected from deuterium, $C_1$ to $C_{12}$ alkyl and $C_1$ to $C_{12}$ alkoxy.

According to another embodiment $R^1$, $R^2$, $R^3$, $R^4$ and $R^5$ may be independently selected from unsubstituted or substituted $C_6$ aryl and unsubstituted or substituted pyridyl; and the substituents are selected from deuterium, $C_1$ to $C_{12}$ alkyl and $C_1$ to $C_{12}$ alkoxy.

According to another embodiment $R^1$, $R^2$, $R^3$, $R^4$ and $R^5$ may be independently selected from unsubstituted or substituted $C_6$ to $C_{12}$ aryl and unsubstituted or substituted pyridyl; and the substituents are selected from deuterium, $C_1$ to $C_6$ alkyl and $C_1$ to $C_6$ alkoxy.

According to another embodiment $R^1$, $R^2$, $R^3$, $R^4$ and $R^5$ may be independently selected from unsubstituted or substituted $C_6$ aryl and unsubstituted or substituted pyridyl; and the substituents are selected from deuterium, $C_1$ to $C_6$ alkyl and $C_1$ to $C_6$ alkoxy.

According to another embodiment $R^1$, $R^2$, $R^3$, $R^4$ and $R^5$ may be independently selected from unsubstituted or substituted $C_6$ to $C_{12}$ aryl and unsubstituted or substituted pyridyl; and the substituents are selected from deuterium, $C_2$ to $C_6$ alkyl and $C_2$ to $C_6$ alkoxy.

According to another embodiment $R^1$, $R^2$, $R^3$, $R^4$ and $R^5$ may be independently selected from unsubstituted or substituted $C_6$ aryl and unsubstituted or substituted pyridyl; and the substituents are selected from deuterium, $C_3$ to $C_5$ alkyl and $C_3$ to $C_5$ alkoxy.

According to another embodiment, an organic optoelectronic device includes an anode and a cathode facing each other and at least one organic layer between the anode and the cathode, wherein the organic layer includes the compound for an organic optoelectronic device.

According to yet another embodiment, a display device including the organic optoelectronic device is provided.

According to another aspect a compound of formula (I), is provided wherein

L is selected from phenylene, naphthylene and biphenylene;

$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, b, c, d and e are independently selected from 0 or 1 and 3≤a+b+c+d+e≤5, preferably 4≤a+b+c+d+e≤5 and also preferred, a, b, c, d and e are each selected 1.

In the specification the wording "the substituents are selected from deuterium, $C_1$ to $C_{12}$ alkyl and $C_1$ to $C_{12}$ alkoxy" refers to $R^1$, $R^2$, $R^3$, $R^4$ and $R^5$, if not otherwise stated.

According to another aspect a compound of formula (Ia), is provided:

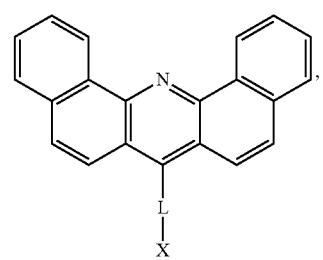

(Ia)

wherein
X has the chemical structure IIa:

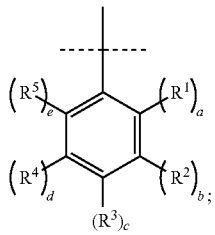

wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, b, c, d and e are independently selected from 0 or 1 and $3 \leq a+b+c+d+e \leq 5$, preferably $4 \leq a+b+c+d+e \leq 5$ and also preferred, a, b, c, d and e are each selected 1.

According to another aspect a compound of formula (I), is provided wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, c and e are each selected 0, and
b and d are each selected 1.

According to another aspect a compound of formula (Ia), is provided:

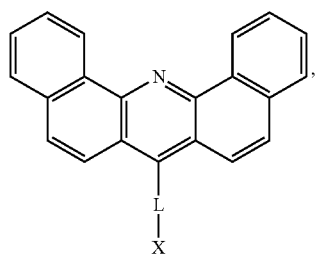

wherein
X has the chemical structure IIb:

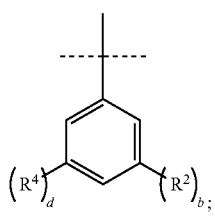

wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
b and d are each selected 1.

According to another aspect a compound of formula (I), is provided wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
c and e are each selected 0, and a, b and d are each selected 1.

According to another aspect a compound of formula (Ia), is provided:

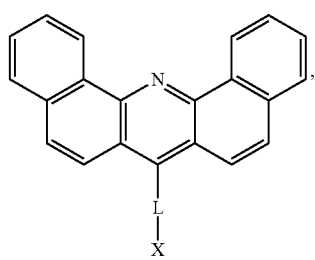

wherein
X has the chemical structure IIc:

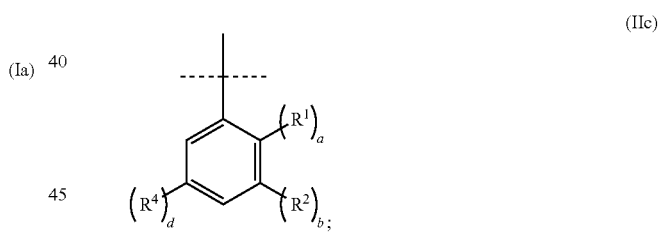

wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, b and d are each selected 1.

According to another aspect a compound of formula (I), is provided wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
e is selected 0, and a, b, c and d are each selected 1.

According to another aspect a compound of formula (Ia), is provided:

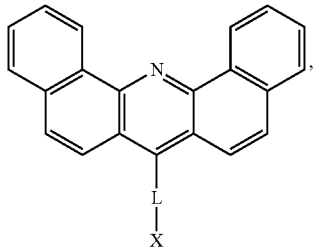
(Ia)

wherein
X has the chemical structure IId:

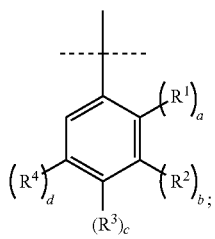
(IId)

wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, b, c and d are each selected 1.

According to another aspect a compound of formula (I), is provided wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a and c are each selected 1, and
b, d and e are each selected 0.

According to another aspect a compound of formula (Ia), is provided:

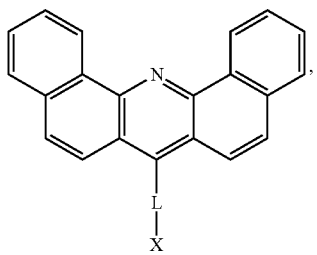
(Ia)

wherein
X has the chemical structure IIe:

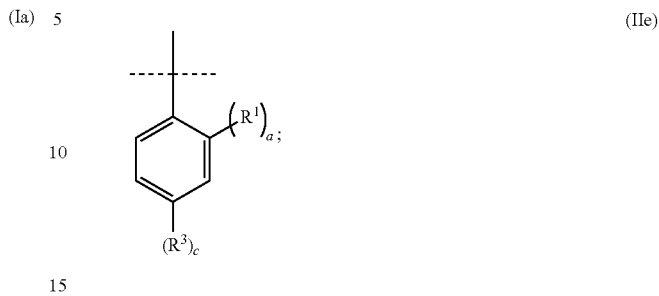
(IIe)

wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a and c are each selected 1.

According to another aspect a compound of formula (I), is provided wherein
L is selected from phenylene, naphthylene and biphenylene; and
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, b and c are each selected 1, and
b, d and e are each selected 0.

According to another aspect a compound of formula (Ia), is provided:

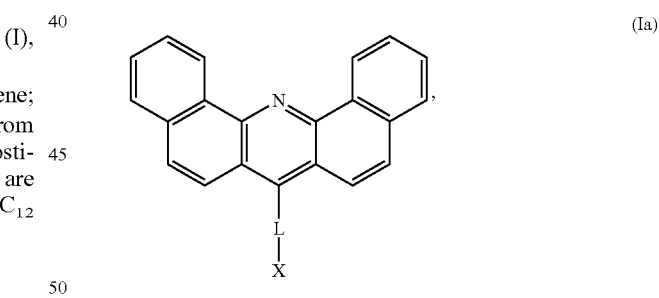
(Ia)

wherein
X has the chemical structure IIf:

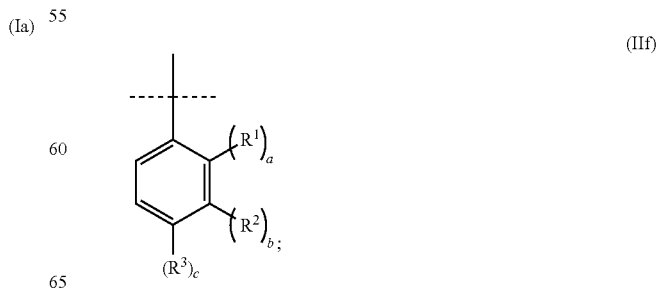
(IIf)

wherein

L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, b and c are each selected 1.

According to another aspect a compound of formula (I), is provided wherein

L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, b, c and e are each selected 1, and is selected 0.

According to another aspect a compound of formula (Ia), is provided:

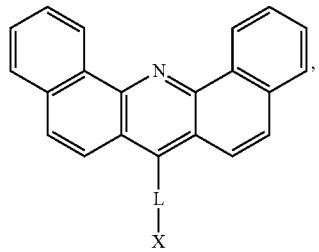

(Ia)

wherein
X has the chemical structure IIg:

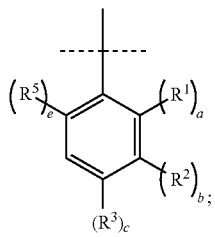

(IIg)

wherein

L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, b, c and e are each selected 1.

According to another aspect a compound of formula (I), is provided wherein

L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a and e are each selected 1, and
b, d and c are each selected 0.

According to another aspect a compound of formula (Ia), is provided:

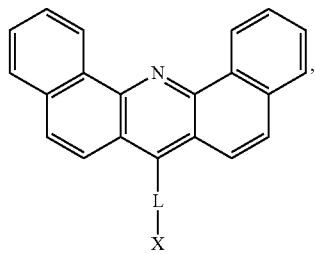

(Ia)

wherein
X has the chemical structure IIh:

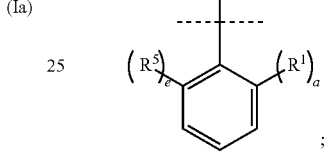

(IIh)

wherein

L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a and e are each selected 1.

According to another aspect a compound of formula (I), is provided wherein

L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, c and e are each selected 1, and
b and d are each selected 0.

According to another aspect a compound of formula (Ia), is provided:

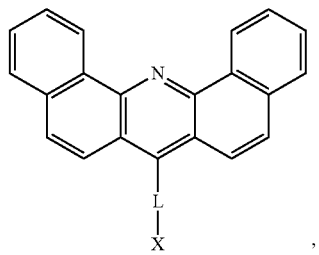

(Ia)

wherein
X has the chemical structure IIi:

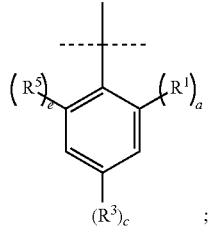

wherein

L is selected from phenylene, naphthylene and biphenylene;

$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and a, c and e are each selected 1.

According to another aspect in formula I the groups $R^1$, $R^2$, $R^3$, $R^4$ and $R^5$ may be independently selected from unsubstituted or substituted $C_6$ to $C_{18}$ aryl, preferably $C_6$ to $C_{12}$ aryl; and preferably, $R^1$, $R^2$, $R^3$, $R^4$ and $R^5$ are selected the same from unsubstituted or substituted $C_6$ to $C_{18}$ aryl; and more preferred $R^1$, $R^2$, $R^3$, $R^4$ and $R^5$ are selected the same from $C_6$ to $C_{12}$ aryl.

Preferably in formula I, L may be selected from phenylene or biphenylene, more preferably L comprises at least one meta linked group. Particularly good performance is achieved, when the compound of formula I is selected in this range.

According to another aspect the compound of formula (I) may be selected from compounds of the group comprising formula (D1) to (D25):

(D1)

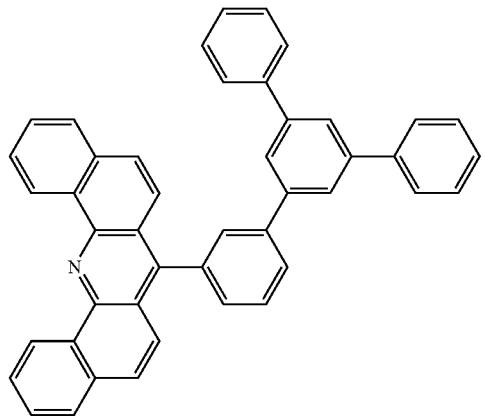

(D2)

(D3)

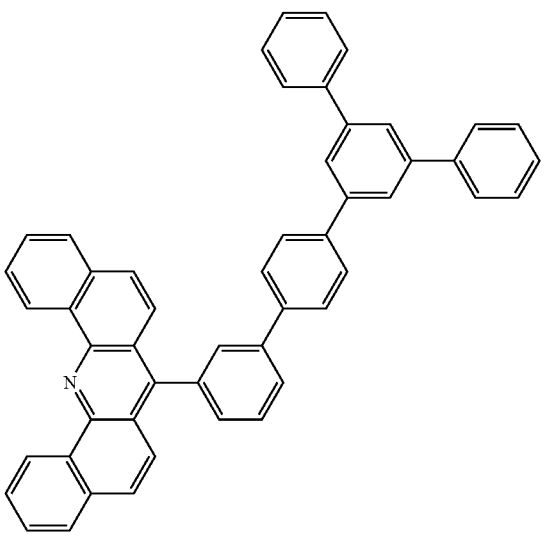

(D4)

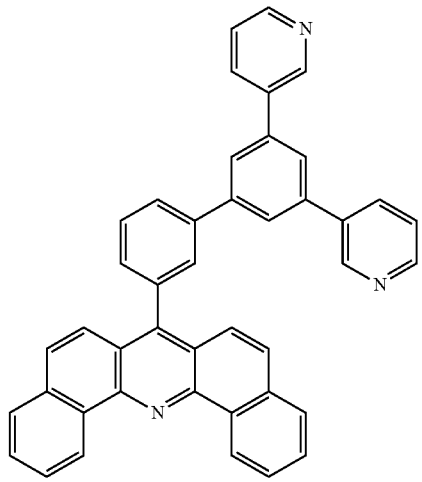

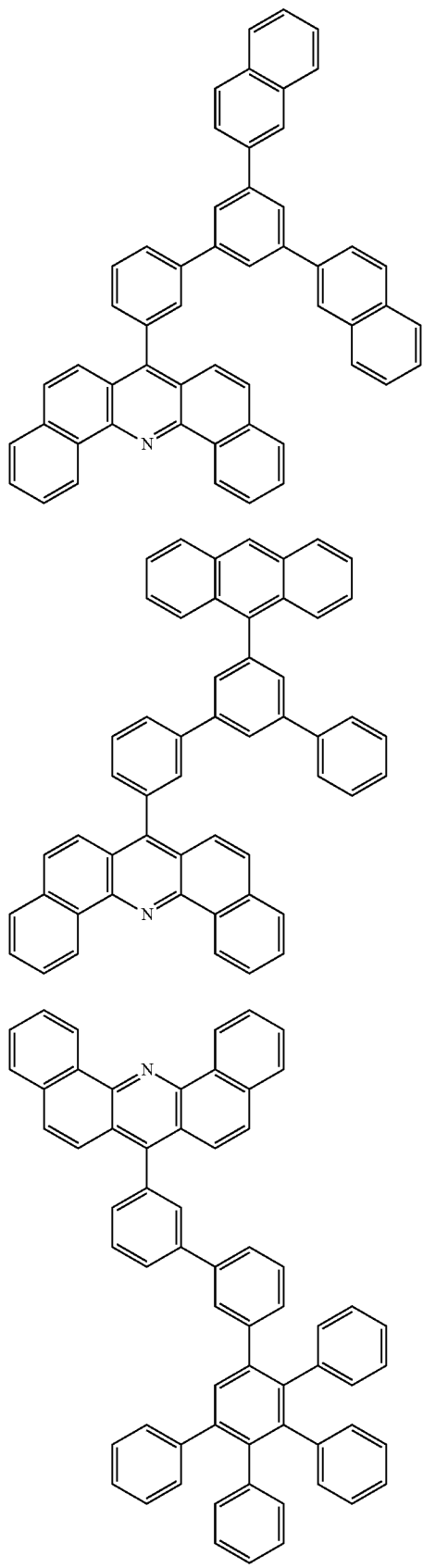
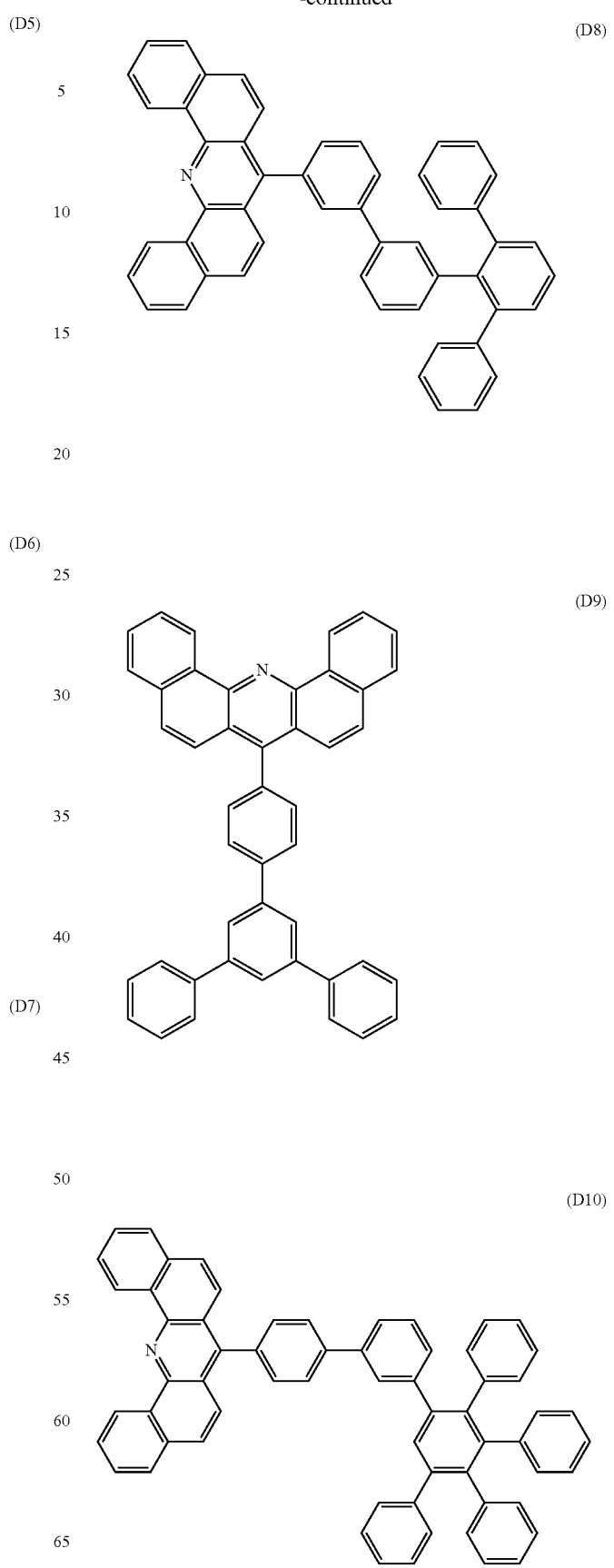

(D11)
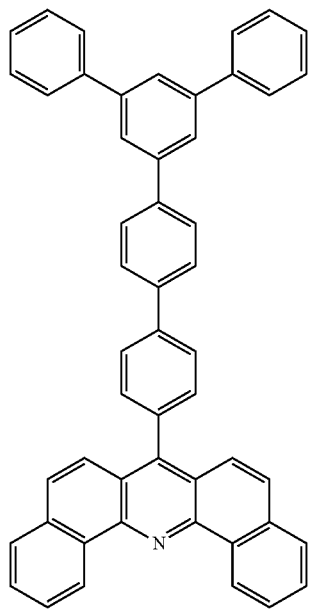
(D12)
(D13)
(D14)
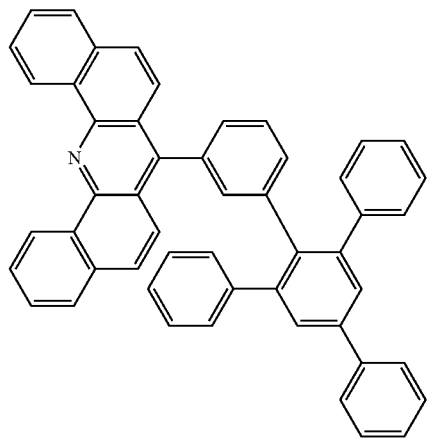
(D15)
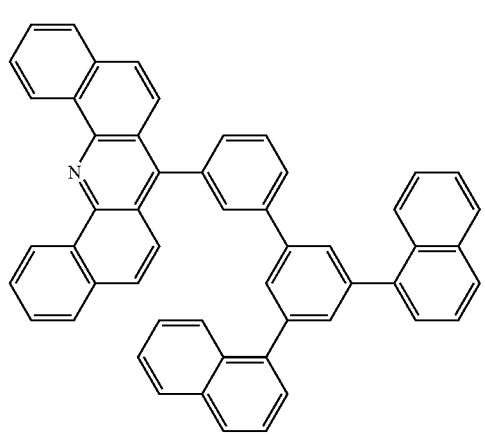
(D16)
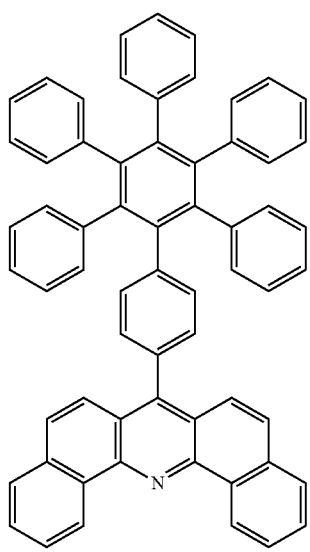

(D17)
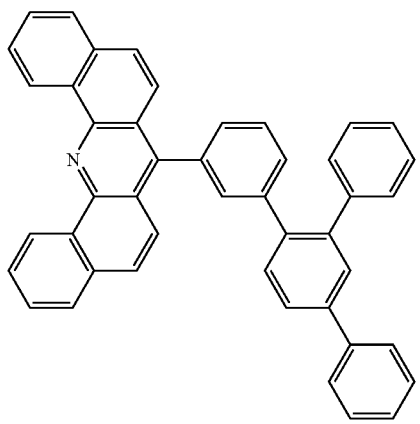
(D18)
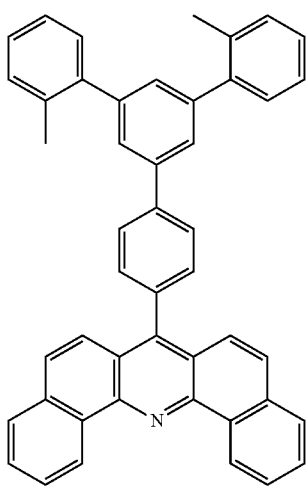
(D19)
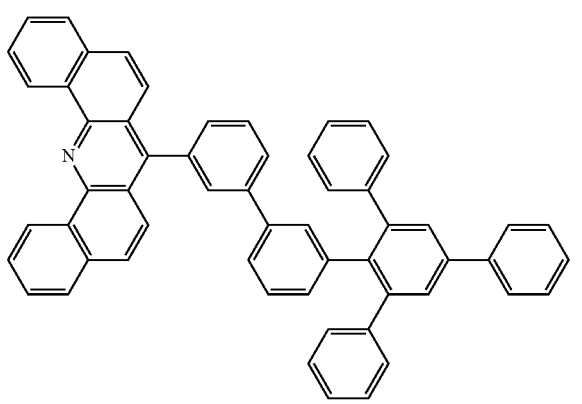
(D20)
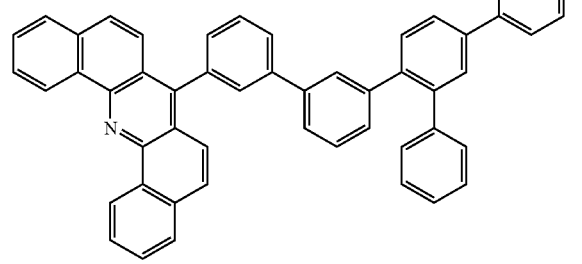
(D21)
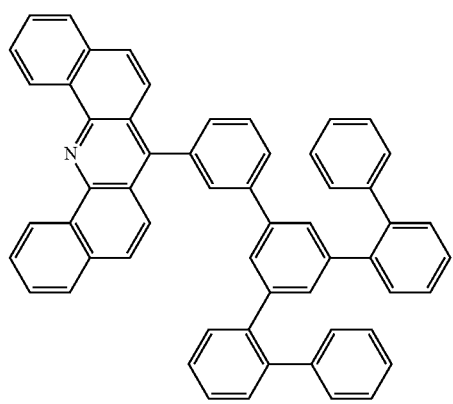
(D22)
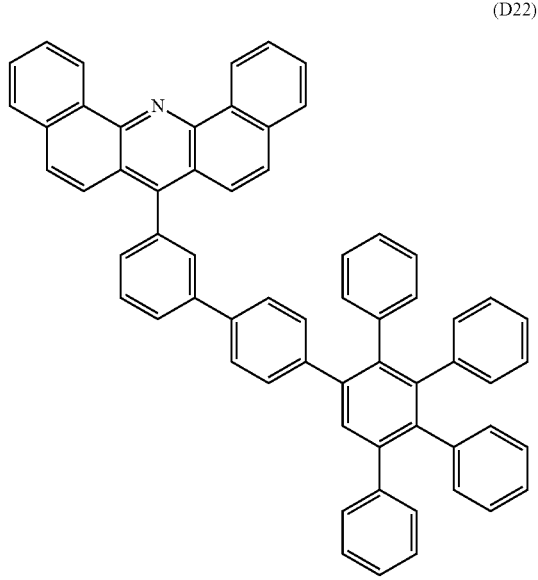
(D23)
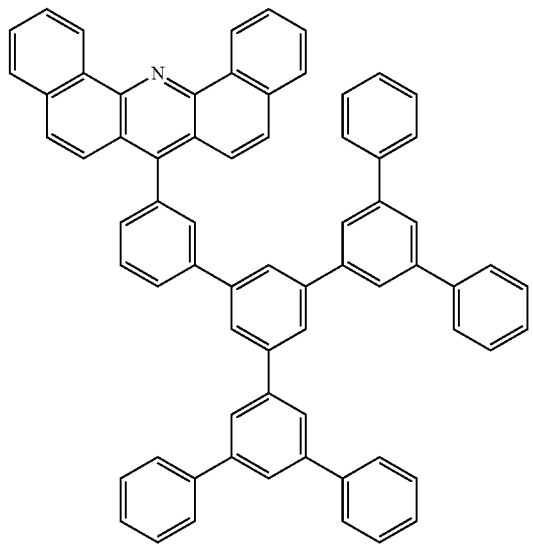

-continued

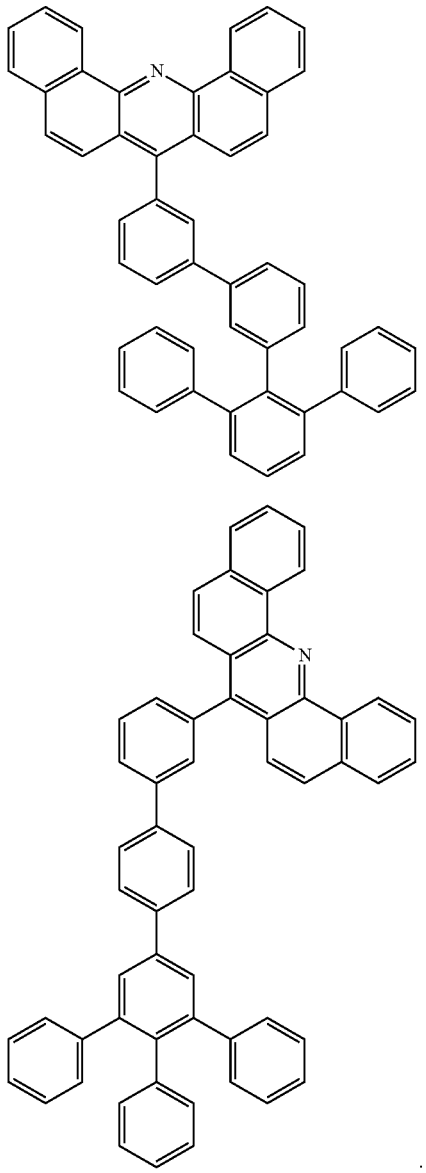

(D24)

(D25)

According to another embodiment an organic semiconductor material comprising the compound of formula (I) is provided.

According to another embodiment an electronic device comprising the compound of formula (I) is provided.

According to another embodiment a device comprising an organic light-emitting diode comprising the compound of formula (I) is provided.

According to another embodiment a display device comprising the compound of formula (I) is provided.

According to another embodiment a method of manufacturing the same is provided.

According to another embodiment, an organic optoelectronic device includes an anode and a cathode facing each other and at least one organic layer between the anode and the cathode, wherein the organic layer includes the compound of formula (I).

According to yet another embodiment, a display device including the organic optoelectronic device is provided.

Advantageous Effects

Surprisingly, it was found that the compounds of formula I and the inventive electronic device solve the problem underlying the present invention by being superior over the organic electroluminescent devices and compounds known in the art, in particular with respect to glass transition temperature and cd/A efficiency. A high glass transition temperature is important for improved thermal stability of a layer formed from the compound of formula I, and thereby improved thermal stability of an electronic device. High cd/A efficiency is important for high efficiency and thereby increased battery life of a mobile device, for example a mobile display device.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned properties of cd/A efficiency. These compounds are discussed herein to be particularly preferred.

Further an organic optoelectronic device having high efficiency long life-span may be realized.

Hereinafter, a compound for an organic optoelectronic device according to an embodiment is described.

A compound for an organic optoelectronic device according to an embodiment is represented by formula I according to the invention.

The compound of the invention of formula I having an acridine structure element may help injection or transport of holes or increases a glass transition temperature of the compound, and thus luminance efficiency may be increased due to suppression of an intermolecular interaction, and the compound may have a low deposition temperature relative to the molecular weight.

Accordingly, when the compound for an organic optoelectronic device represented by formula I forms a film, the compound may facilitate injection and transport of electrons in the device due to excellent packing of the acridine structure element and the aryl groups having a relatively flat structure compared with other bulky aromatic groups. Therefore, when the compound for an organic optoelectronic device represented by formula I is particularly used to form an electron injection auxiliary layer, the compound may decrease a driving voltage of the device due to excellent electron transport characteristics and increase luminous efficiency due to rapid injection of electrons into an emission layer. On the other hand, when the compound is mixed with a material having excellent hole injection and transport characteristics to form the emission layer, the compound may also decrease a driving voltage due to excellent electron transport capability and obtain excellent luminance efficiency due to an intermolecular interaction by the moiety having the bulky aromatic group. In addition, excellent electron injection and transport characteristics of the compound for an organic optoelectronic device represented by formula I may be obtained. In addition, the compound of formula I may still maintain excellent electron injection and transport characteristics even when used to from an electron injection auxiliary layer or to form an emission layer as a mixture with a compound having excellent hole characteristics.

The compound for an organic optoelectronic device represented by formula I may include at least 4 to about 15, preferably at least 5 to about 8, substituted or unsubstituted $C_6$ to $C_{18}$ aryl groups. Particularly good performance characteristics are obtained when the compound of formula I is selected in this range.

The compound for an organic optoelectronic device represented by formula I may have a molecular weight (Mw) of ≥580 to ≤850 g/mol, and preferably ≥580 to ≤830 g/mol. If the molecular weight is selected in this range, particularly reproducible evaporation and deposition can be achieved in vacuum at temperatures where good long-term stability is observed.

In addition, the compound for an organic optoelectronic device represented by formula I may be represented by one of, for example formulae IIa to IIi.

In addition, the compound for an organic optoelectronic device represented by formula I may be represented by one of, for example formulae D1 to D23.

One or more of the compound of formula I, formulae IIa to IIi and/or formulae D1 to D23 for an organic optoelectronic device may be used.

According to another aspect, the compound of formula I may have a glass transition temperature (Tg) selected between ≤122 and ≤200° C., preferably ≤122 and ≤180° C., also preferred ≤125 and ≤180° C., further preferred ≤130 and ≤180° C.

The glass transition temperature is measured under nitrogen and using a heating rate of 10 K per min in a Mettler Toledo DSC 822e differential scanning calorimeter as described in DIN EN ISO 11357, published in March 2010.

Preferably, the compound of formula I is essentially non-emissive.

In the context of the present specification the term "essentially non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the dipole moment of the compound of formula I may be selected ≥0 and ≤2.8 Debye, preferably ≥0.8 and ≤2.75 Debye, also preferred ≥0.8 and ≤2 Debye. Particularly good performance is obtained when the compound of formula I is selected in this range.

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The values in Table 1 were calculated using the method as described below.

The partial charges and atomic positions are obtained using either the DFT functional of Becke and Perdew BP with a def-SV(P) basis or the hybrid functional B3LYP with a def2-TZVP basis set as implemented in the program package TURBOMOLE V6.5. If more than one conformation is viable, the conformation with the lowest total energy is selected to determine the dipole moment.

According to another aspect, the reduction potential of the compound of formula I may be selected more negative than −2.2 V and less negative than −2.35 V against Fc/Fc⁺ in tetrahydrofuran, preferably more negative than −2.25 V and less negative than −2.3 V.

The reduction potential may be determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc⁺/Fc redox couple, afforded finally the values reported above. All studied compounds as well as the reported comparative compounds showed well-defined reversible electrochemical behaviour.

According to another embodiment the organic semiconductor material may comprises a compound of formula (I), formulae IIa to IIi and/or formulae D1 to D23.

According to another embodiment the organic semiconductor material may comprises further an alkali halide and/or alkali organic complex.

Preferably, the organic semiconductor material is essentially non-emissive.

According to another embodiment the organic semiconductor layer may comprises a compound of formula (I), formulae IIa to IIi and/or formulae D1 to D23.

According to another embodiment the organic semiconductor layer may comprises in addition an alkali halide and/or alkali organic complex.

According to another embodiment an electronic device may comprises a compound of formula (I), formulae IIa to IIi and/or formulae D1 to D23.

According to another embodiment the electronic device can be an organic electroluminescent device, preferably the electronic device is a display device.

According to another embodiment the electronic device can be an organic photovoltaic device, organic thin film transistor or an organic battery.

According to another embodiment the electronic device comprises an organic semiconductor layer, preferably an electron transport layer, comprising the compound according to formula (I), formulae IIa to IIi and/or formulae D1 to D23, preferably the organic semiconductor layer is arranged between the emission layer and the cathode electrode.

Preferably, the semiconductor layer is arranged between the emission layer and the cathode and is essentially non-emissive.

Preferably, the semiconductor layer is arranged between the emission layer and the cathode and is essentially non-emissive, wherein the semiconductor layer, the emission layer and the cathode may differ in their components and composition.

According to another embodiment, the organic semiconductor layer comprising the compound of formula I is in direct contact with the cathode electrode.

According to another embodiment, the organic semiconductor layer comprising the compound of formula I is in direct contact with the emission layer.

According to another embodiment, the organic semiconductor layer comprising the compound of formula I is in direct contact with the electron transport auxiliary layer.

According to another embodiment, the organic semiconductor layer comprising the compound of formula I is in direct contact with the electron injection layer.

According to another embodiment, the organic semiconductor layer comprising the compound of formula I is contacting sandwiched between the electron transport auxiliary layer and the electron injection layer.

According to another embodiment, the organic semiconductor layer comprising the compound of formula I is contacting sandwiched between the electron transport auxiliary layer and the electron injection layer and the organic semiconductor layer further comprises an alkali halide or alkali organic complex.

According to another embodiment, the organic semiconductor layer comprising the compound of formula I is contacting sandwiched between the electron transport auxiliary layer and the cathode electrode.

According to another embodiment, the organic semiconductor layer comprising the compound of formula I is contacting sandwiched between the electron transport auxiliary layer and the cathode electrode and the organic semiconductor layer further comprises an alkali halide or alkali organic complex.

Hereinafter, an organic optoelectronic device according to another embodiment is described.

An organic optoelectronic device according to another embodiment includes an anode and a cathode facing each other and at least one organic layer between the anode and the cathode and the organic layer includes the compound for an organic optoelectronic device.

The compound for an organic optoelectronic device represented by formula I may be appropriate for an organic layer of an organic optoelectronic device, for example, a host of an emission layer or an electron transport auxiliary layer of the organic layer.

The organic optoelectronic device may realize a low driving voltage, high efficiency, high luminance and long life-span by including the organic layer including the compound for an organic optoelectronic device.

Figure 1:
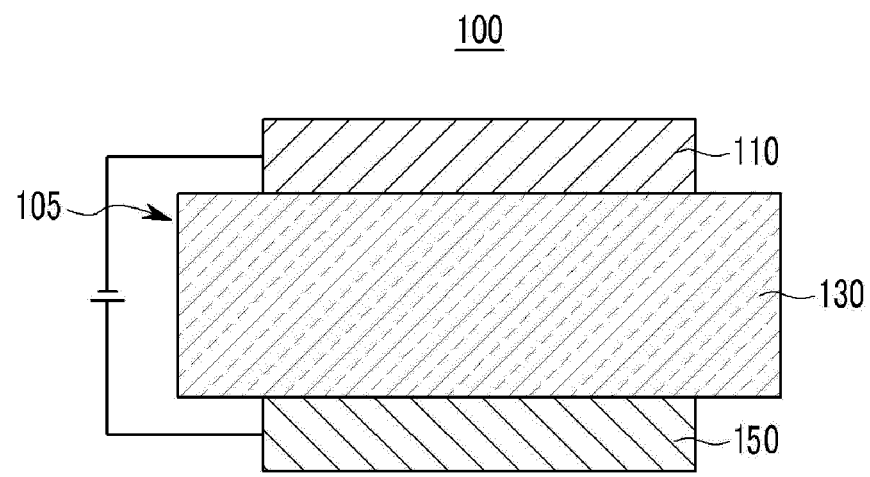
FIG. 1 is a cross-sectional view showing an organic light emitting diode according to an embodiment.

The compound for an organic optoelectronic device represented by formula I may be appropriate for an organic layer of an organic optoelectronic device, for example, a host of an emission layer or an electron transport auxiliary layer of the organic layer.

The organic optoelectronic device may realize a low driving voltage, high efficiency, high luminance and long life-span by including the organic layer including the compound for an organic optoelectronic device.

Hereinafter, the figures are illustrated in more detail with reference to examples. However, the present disclosure is not limited to the following figures.

FIGS. 1 to 4 are schematic cross-sectional views of organic light emitting diodes 100, 200, 300, and 400 according to an embodiment of the present invention. Hereinafter, referring to FIG. 1, a structure of an organic light emitting diode according to an embodiment of the present invention and a method of manufacturing the same are as follows. The organic light emitting diode 100 has a structure where a cathode 110, an organic layer 105 including an optional hole transport region; an emission layer 130 comprising a compound according to formula I; and an anode 150 that are sequentially stacked.

A substrate may be further disposed under the cathode 110 or on the anode 150. The substrate may be a substrate that used in a general organic light emitting diode and may be a glass substrate or a transparent plastic substrate with strong mechanical strength, thermal stability, transparency, surface smoothness, ease of handling, and water resistance.

The anode 150 may be formed by depositing or sputtering an anode material on a substrate. The anode material may be selected from materials having a high work function that makes hole injection easy. The anode 150 may be a reflective electrode, a transflective electrode, or a transmissive electrode. The anode material may use indium tin oxide (ITO), indium zinc oxide (IZO), tin oxide ($SnO_2$), zinc oxide (ZnO), and the like. Or, it may be a metal such as magnesium (Mg), aluminum (Al), aluminum-lithium (Al—Li), calcium (Ca), magnesium-indium (Mg—In), or magnesium-silver (Mg—Ag).

The anode 150 may have a monolayer or a multi-layer structure of two or more layers.

The organic light emitting diodes 100, 200, 300, and 400 according to an embodiment of the present invention may include a hole transport region; an emission layer 120; and an electron transport auxiliary layer 135 comprising a compound according to formula I.

Figure 2:
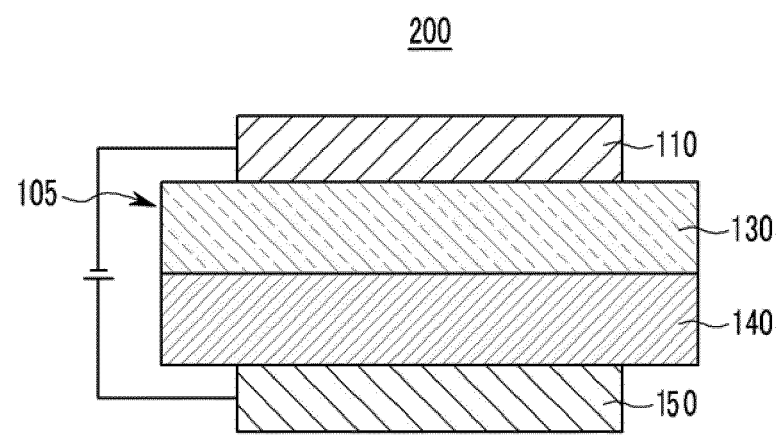
FIG. 2 is a cross-sectional view specifically showing an organic layer of an organic light emitting diode according to an embodiment.

For example, referring to FIG. 2, an organic light emitting diode according to an embodiment of the present invention is described. The organic light emitting diodes 100, 200, 300, and 400 according to an embodiment of the present invention may include further a hole auxiliary layer 140 between the anode 120 and the emission layer 130.

Figure 3:
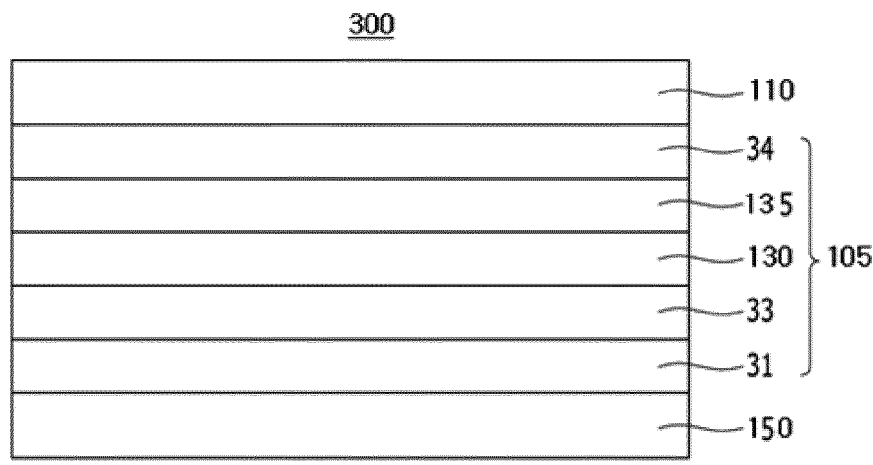
FIGS. 3 and 4 are cross-sectional views specifically showing a part of an organic layer of an organic light emitting diode according to an embodiment.

Referring to FIG. 3, the hole transport region 105 may include at least two layered hole auxiliary layer, and in this case, a hole auxiliary layer contacting the emission layer is defined as a hole transport auxiliary layer 33 and a hole auxiliary layer contacting an anode is defined as a hole transport layer 31 as well as two electron transport layer of electron transport auxiliary layer 135/electron transport layer 34. The hole transport region may include at least one of a hole injection layer, a hole transport layer, an electron blocking layer, and a buffer layer.

The hole transport region may include only hole injection layer or only hole transport layer. Or, the hole transport region may have a structure where a hole injection layer 37/hole transport layer 31 or hole injection layer 37/hole transport layer 31/electron blocking layer is sequentially stacked from the anode 120.

Figure 4:
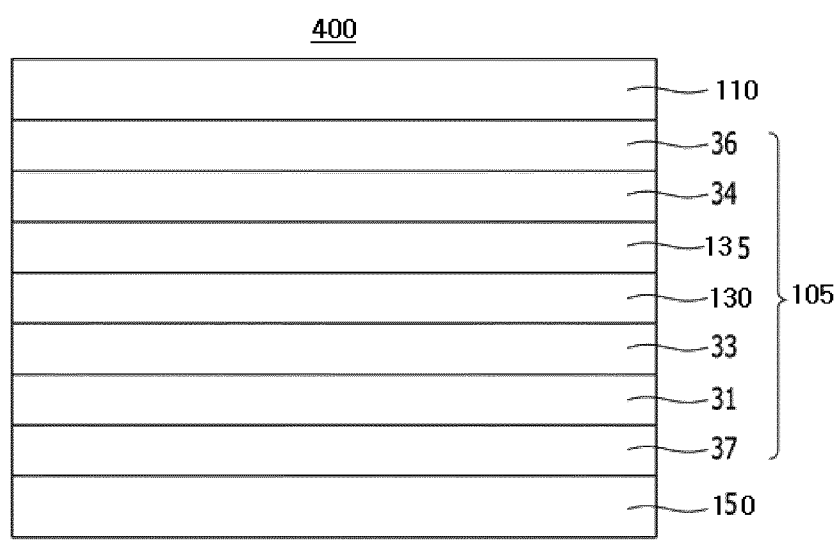

For example, the hole injection layer 37 and the electron injection layer 36 are additionally included and as shown in FIG. 4, anode 120/hole injection layer 37/hole transport layer 31/hole transport auxiliary layer 33/emission layer 130/electron transport auxiliary layer 135 comprising a compound according formula I/electron transport layer 34/electron injection layer 37/anode 110 are sequentially stacked.

In another example, the hole injection layer 37 and the electron injection layer 36 are additionally included and as shown in FIG. 4, anode 120/hole injection layer 37/hole transport layer 31/hole transport auxiliary layer 33/emission layer 130/electron transport auxiliary layer 135/electron transport layer 34 comprising a compound according formula I/electron injection layer 37/anode 110 are sequentially stacked.

The hole injection layer 37 may improve interface properties between ITO as an anode and an organic material used for the hole transport layer 31, and is applied on a non-planarized ITO and thus planarizes the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31.

When the hole transport region includes a hole injection layer 37, the hole injection layer may be formed on the anode 150 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

Compound HT-D1

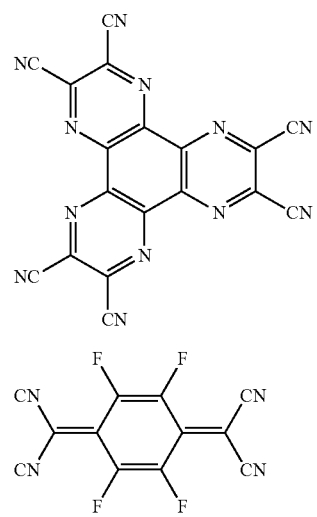

F4-TCNQ

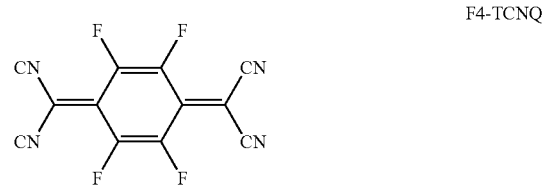

The hole transport region may further include a buffer layer.

The buffer layer may compensate for an optical resonance distance of light according to a wavelength of the light emitted from the EML, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include a host and a dopant.

For example, the composition comprising compound of formula I may be used as a light-emitting material for an organic optoelectronic device. Herein, the compound of formula I may be the emitter host (also named EML host), and may further include at least one dopant. The dopant may be a red, green, or blue dopant.

Preferably, the emitter host is an anthracene matrix compound represented by formula 400 below:

Formula 400

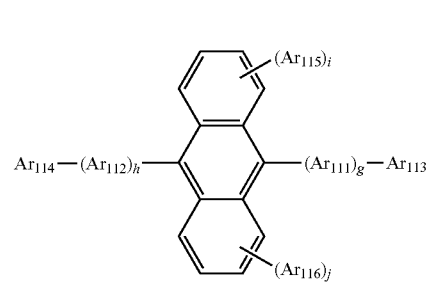

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ aryl group; and g, h, i, and j may be each independently an integer from 0 to 4.

In some embodiments, $Ar_{111}$ and $Ar_{112}$ in formula 400 may be each independently one of a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of
a $C_1$-$C_{10}$ alkyl group substituted with at least one of a phenyl group, a naphthyl group, or an anthryl group;
a phenyl group, a naphthyl group, an anthryl group, a pyrenyl group, a phenanthrenyl group, or a fluorenyl group;
a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof,
a sulfonic acid group or a salt thereof, a phosphoric acid group or a salt thereof,
a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or
a fluorenyl group; or

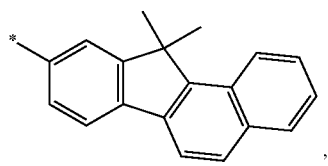 [SMILES: *c1ccc2c(c1)C(C)(C)c1c-2ccc2ccccc12]

or formulas (2) or (3)

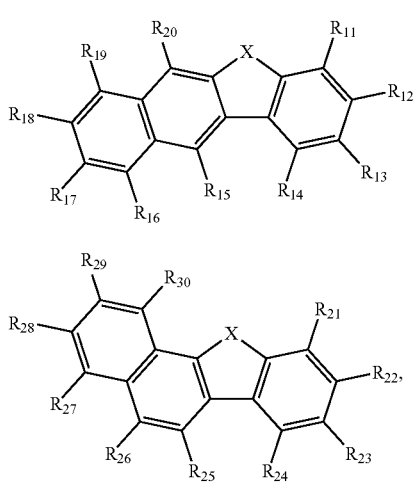

Wherein in the formulas (2) and (3), X is selected form an oxygen atom and a sulfur atom, but embodiments of the invention are not limited thereto.

In the formula (2), any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula (3), any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Preferably, the dipole moment of the EML host is selected $\geq 0.2$ Debye and $\leq 1.45$ Debye, preferably $\geq 0.4$ Debye and $\leq 1.2$ Debye, also preferred $\geq 0.6$ Debye and $\leq 1.1$ Debye.

The dipole moment is calculated using the optimized using the hybrid functional B3LYP with the 6-31G* basis set as implemented in the program package TURBOMOLE V6.5. If more than one conformation is viable, the conformation with the lowest total energy is selected to determine the dipole moment of the molecules. Using this method, 2-(10-phenyl-9-anthracenyl)-benzo[b]naphtho[2,3-d]furan (CAS 1627916-48-6) has a dipole moment of 0.88 Debye, 2-(6-(10-phenylanthracen-9-yl)naphthalen-2-yl)dibenzo[b,d]thiophene (CAS 1838604-62-8) of 0.89 Debye, 2-(6-(10-phenylanthracen-9-yl)naphthalen-2-yl)dibenzo[b,d]furan (CAS 1842354-89-5) of 0.69 Debye, 2-(7-(phenanthren-9-yl)tetraphen-12-yl)dibenzo[b,d]furan (CAS 1965338-95-7) of 0.64 Debye, 4-(4-(7-(naphthalen-1-yl)tetraphen-12-yl)phenyl) dibenzo[b,d] furan (CAS 1965338-96-8) of 1.01 Debye.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a fluorescent dopant, for example ter-fluorene, the structures are shown below. 4,4'-bis(4-diphenyl amiostyryl)biphenyl (DPAVBi), 2,5,8,11-tetra-tert-butyl perylene (TBPe), and Compound 4 below are examples of fluorescent blue dopants.

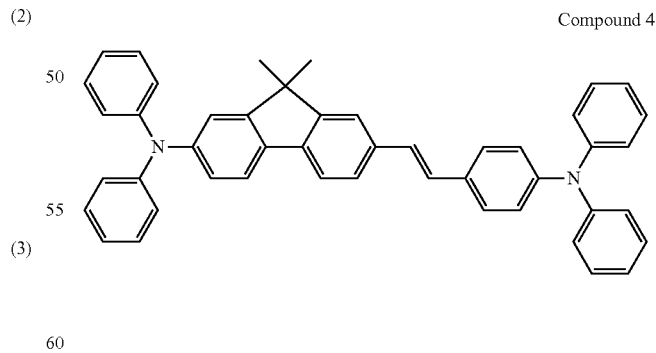

Compound 4

According to another aspect, the organic semiconductor layer comprising a compound of formula I is arranged between a fluorescent blue emission layer and the cathode electrode.

The dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

L$_2$MX(Z).

In formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

A thickness of the emission layer may be about 100 Å to about 1000 Å, for example about 200 Å to about 600 Å. When the thickness of the emission layer is within these ranges, the emission layer may have improved emission characteristics without a substantial increase in a driving voltage.

Next, an electron transport region is disposed on the emission layer.

The electron transport region may include at least one of a electron transport auxiliary layer, an electron transport layer, and an electron injection layer.

For example, the electron transport region may have a structure of a electron transport auxiliary layer/electron transport layer/electron injection layer or electron transport layer/electron injection layer, but is not limited thereto. For example, an organic light emitting diode according to an embodiment of the present invention includes at least two electron transport layers in the electron transport region, and in this case, an electron transport layer contacting the emission layer is defined as an electron transport auxiliary layer 135.

The electron transport layer may have a monolayer or multi-layer structure including two or more different materials.

The electron transport region may include the compound for an organic optoelectronic device represented by formula I. For example, the electron transport region may include an electron transport layer, and the electron transport layer may include the compound for an organic optoelectronic device represented by formula I. More specifically, the electron transport auxiliary layer 135 may include the compound for an organic optoelectronic device represented by formula I.

According to one aspect of the present invention, the electron transport auxiliary layer (a-ETL) 135 comprises a compound according to formula I.

According to another aspect of the present invention, the electron transport auxiliary layer 135 consists of compound of formula I.

The formation conditions of the electron transport auxiliary layer 135, electron transport layer (ETL) 34, and electron injection layer 36 of the electron transport region refers to the formation condition of the hole injection layer.

When the electron transport region includes the electron transport auxiliary layer 135, the electron transport auxiliary layer may include at least one of BCP, Bphen, and BAlq, but is not limited thereto.

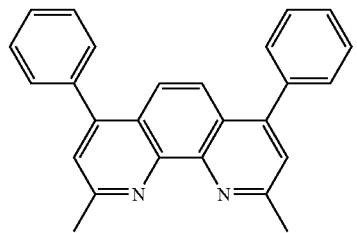

BCP

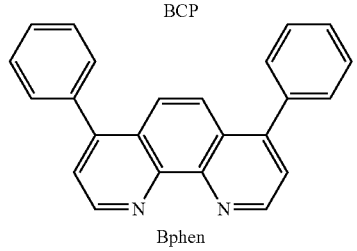

Bphen

The thickness of the electron transport auxiliary layer may be from about 20 Å to about 1000 Å, for example about 30 Å to about 300 Å. When the thickness of the electron transport auxiliary layer is within these ranges, the electron transport auxiliary layer may have improved electron transport auxiliary ability without a substantial increase in driving voltage.

According to another aspect of the present invention, the electron transport layer (ETL) 34 comprises a compound of formula I.

According to another aspect of the present invention, the electron transport layer 34 comprises a compound of formula I and further comprises an alkali halide and/or alkali organic complex.

The electron transport layer 34 may further include at least one of the BCP, Bphen and the following Alq$_3$, Balq, TAZ and NTAZ;

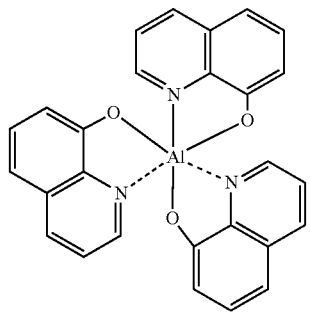

Alq$_3$

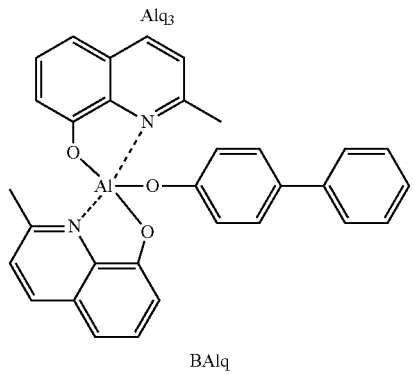

BAlq

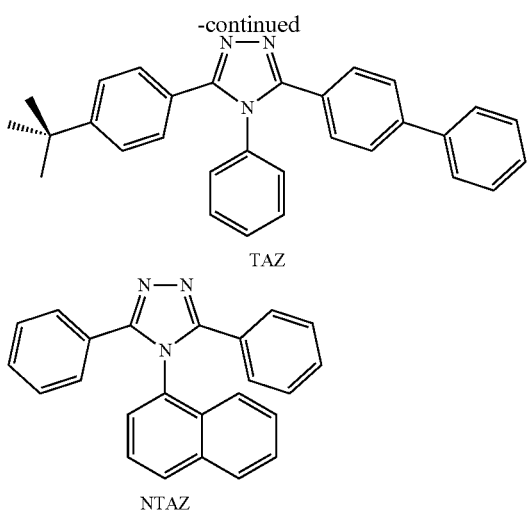

TAZ

NTAZ or, the electron transport layer may include at least one of the following compounds ET1 and ET2, but is not limited thereto:

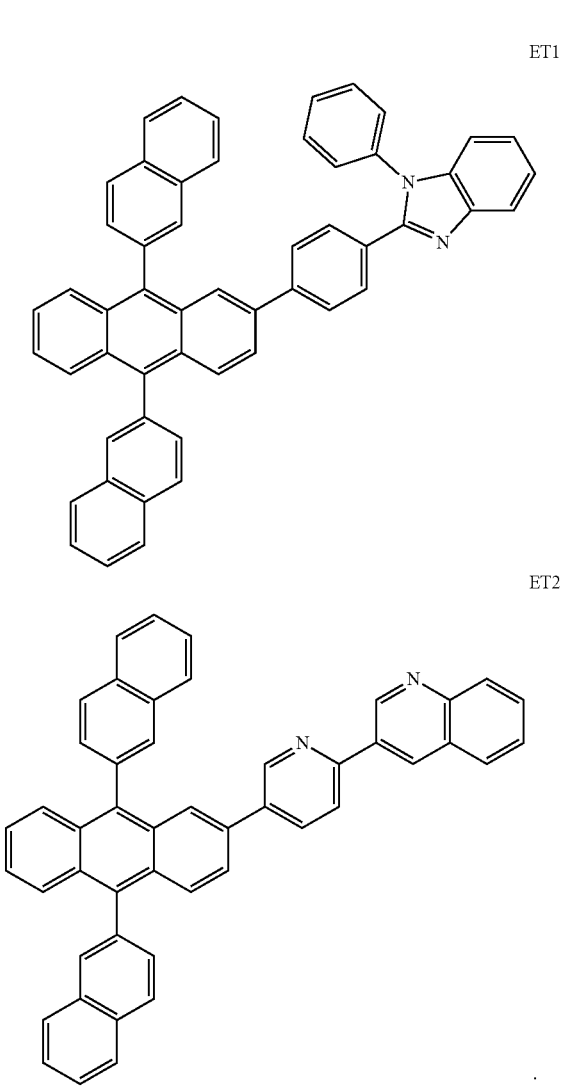

ET1

ET2

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in driving voltage.

The electron transport layer 34 may further include an alkali metal halide and/or alkali organic complex, in addition to the above-described materials. Preferably, the electron transport layer 34 comprises an alkali organic complex.

The alkali organic complex may include a lithium (Li) organic complex. The Li complex may include, for example, the following compound ET-D1 (lithium quinolate, LiQ) or ET-D2.

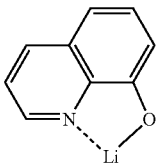

ET-D1

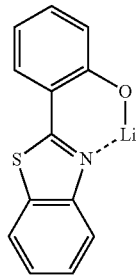

ET-D2

The alkali halide may be selected from the group consisting of LiF, LiCl, LiBr, LiI NaF, NaCl, NaBr, NaI, KF, KBr and CsF.

In addition, the electron transport region may include an electron injection layer (EIL) 36 that may facilitate injection of electrons from the anode 110. The electron injection layer 36 is disposed on an electron transport layer and may play a role of facilitating an electron injection from a cathode and ultimately improving power efficiency and be formed by using any material used in a related art without a particular limit, for example, LiF, Liq, NaCl, CsF, Li$_2$O, BaO, Yb and the like.

The electron injection layer may include at least one selected from LiF, NaCl, CsF, Li$_2$O, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in driving voltage.

The anode 150 is disposed on the organic layer 105. A material for the anode 150 may be a metal, an alloy, or an electrically conductive compound that have a low work function, or a combination thereof. Specific examples of the material for the anode 150 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device, the anode 150 may be formed as a transmissive electrode from, for example, indium tin oxide (ITO) or indium zinc oxide (IZO).

According to another aspect of the invention, a method of manufacturing an organic electroluminescent device (400) is provided, wherein
- on an anode electrode the other layers of hole injection layer (37), hole transport layer (31), optional an electron blocking layer (33), an emission layer (130), first electron transport layer (135), second electron transport layer (34), electron injection layer (36), and a cathode (110), are deposited in that order; or
- the layers are deposited the other way around, starting with the cathode (110).

Hereinafter, the embodiments are illustrated in more detail with reference to examples. However, the present disclosure is not limited to the following examples.

DETAILED DESCRIPTION

Synthesis and Physical Properties

Compounds of formula (I) may be synthesized in accordance with the methods described in WO2011154131A1, *Recent advances in Sonogashira reactions*. R. Chinchilla; C. Nájera, *Chem. Soc. Rev.* 2011, 40, 5084-5121 and *Synthesis of large polycyclic aromatic hydrocarbons: variation of size and periphery*. F. Doetz; J. Diedrich Brand; S. Ito, L. Gherghel; K. Muellen, *J. Am. Chem. Soc.* 2000, 122, 7707-7717.

As a first example, the synthesis of ETM-2 is described:

Step 1: Synthesis of 7-(3-(4,4,5,5-tetramethyl-1,3,2-dioxaborolan-2-yl)phenyl)dibenzo[c,h]acridine

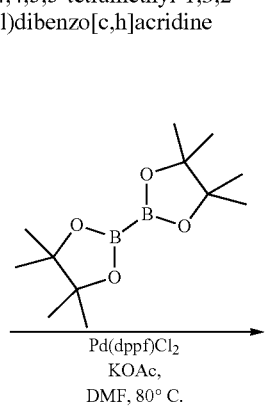
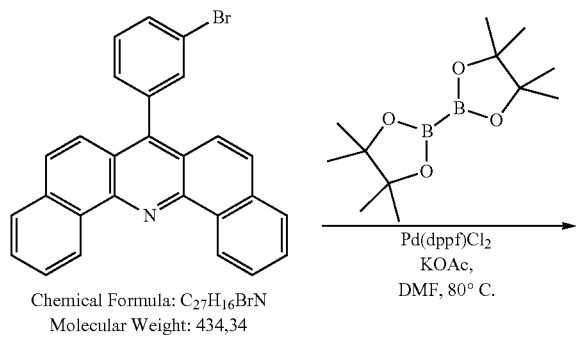
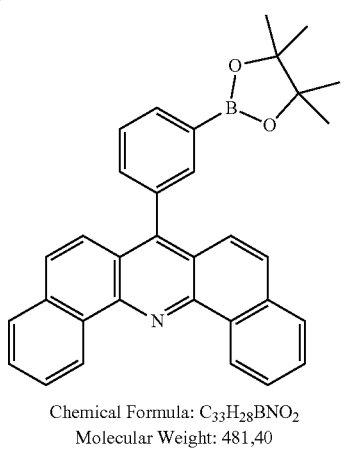

Chemical Formula: C$_{27}$H$_{16}$BrN
Molecular Weight: 434,34

Chemical Formula: C$_{33}$H$_{28}$BNO$_2$
Molecular Weight: 481,40

A three necked 2-L round bottom flask is purged with N$_2$. Under a constant flow of N$_2$ 7-(3-bromophenyl)dibenzo[c,h]acridine (29.5 g, 67.9 mmol) and 4,4,4',4',5,5,5',5'-octamethyl-2,2'-bi(1,3,2-dioxaborolane) (22.42 g, 88.3 mmol, 1.3 eq.) are introduced. DMF (680 mL) is then transferred to the flask using double sided cannula, followed by an addition of potassium acetate (20.0 g, 0.2 mol, 3.0 eq.) and [1,1'-Bis(diphenylphosphino)ferrocene]dichloropalladium(II) (1.49 g, 2 mmol, 0.03 eq.) in a nitrogen flow. Obtained yellow-orange suspension is stirred at 80° C. for 3 days (TLC (SiO$_2$, Hexane/DCM 3:2) shows full consumption of starting compound). The brownish suspension is cooled down to room temperature, a product is separated from the reaction mixture by filtration (frit pore size 4). A filter cake, containing a product, is washed with DMF (2×20 mL), then several times with water (700 mL in total), ethanol (2×60 mL) and dried on the filter. The crude product (~32 g) is dissolved in chloroform (1 L), the solution is passed through a short pad of silica gel (frit pore size 4, silica gel pad: diameter 10 cm, height 5 cm, soaked with CHCl$_3$). The silica pad is rinsed with chloroform (600 mL), the combined organic fractions are concentrated using a rotatory evaporator to a volume of about 50 mL. Resulting suspension is cooled with an ice bath for 30 min to complete precipitation. The product is separated by vacuum filtration (frit pore size 4), rinsed with 2×30 mL hexane and dried in a vacuum at 40° C. overnight.

Yield: about 28.8 g (about 88%, white solid).

Step 2: 7-(5'-phenyl-[1,1':3',1''-terphenyl]-3-yl)dibenzo[c,h]acridine

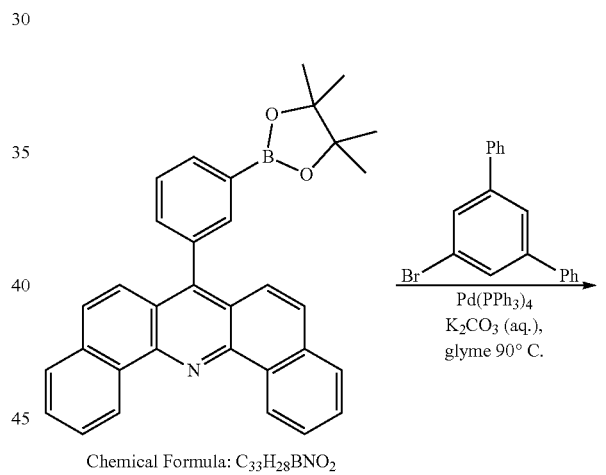
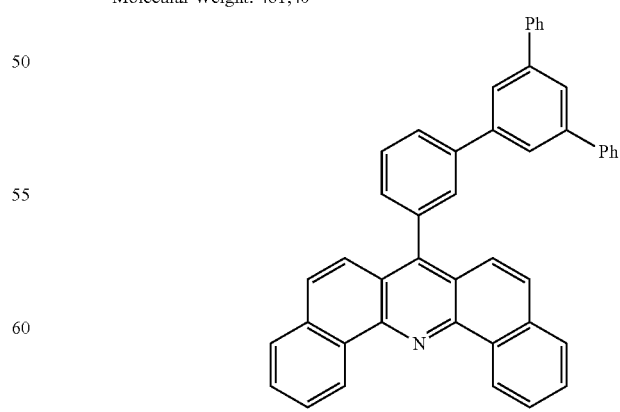

Chemical Formula: C$_{45}$H$_{29}$N
Molecular Weight: 583,73

Potassium carbonate (7.1 g, 51.4 mmol, 3.0 eq.) is dissolved in ~25 of deionized water, the solution is degassed by bubbling $N_2$ for 30 min. Glyme (175 mL) is degassed in 500-mL 3-necked round bottom flask by bubbling $N_2$ for 30 min. The flask is then charged with 7-(3-(4,4,5,5-tetramethyl-1,3,2-dioxaborolan-2-yl)phenyl)dibenzo[c,h]acridine (8.25 g, 17.14 mmol), 5'-bromo-1,1':3',1''-terphenyl (5.56 g, 17.99 mmol, 1.05 eq.) and tetrakis(triphenylphosphin)palladium(0) (0.59 g, 0.51 mmol, 0.03 eq.), which were then added in nitrogen flow. The degassed potassium carbonate solution is added via syringe, nitrogen purged reflux condenser is attached and the reaction mixture heated to 90° C. with stirring for 12 h. The mixture is allowed to cool down to room temperature, a product is collected by filtration (sintered glass filter, pore 4) and washed with water. The traces of Pd-catalyst were removed by treatment of the crude product with ~0.5% aqueous solution of sodium diethyldithiocarbamate (~500 mL) for 1 h. The product is separated by filtration, washed with deionized water (2×400 mL) and methanol (300 mL), and then suspended in boiling methanol, filtered hot and dried. Crude product (~9 g) was triturated with hot toluene, separated by filtration and dried on filter, giving first crop of pure product (4.8 g). Filtrate was concentrated to a volume of ~100 mL, diluted with hexane (50 mL). Precipitated product (second crop) was collected by filtration and dried on filter (2.26 g). The crops were combined and dried at 40° C. in vacuum overnight.

Yield: about 6.78 g (about 68%, off-white solid)

As a second example, the synthesis of ETM-17 is described:

Step 1: Synthesis of 7-(4-(phenylethynyl)phenyl) dibenzo[c,h]acridine

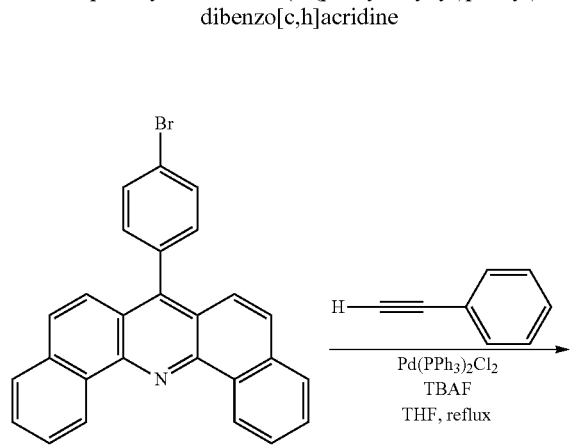

Chemical Formula: $C_{27}H_{16}BrN$
Molecular Weight: 434.34

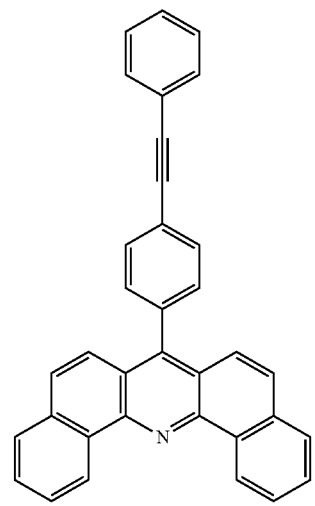

Chemical Formula: $C_{35}H_{21}N$
Molecular Weight: 455.56

A three necked 250-mL round bottom flask is purged with $N_2$. Under a constant flow of $N_2$ 7-(4-bromophenyl)dibenzo[c,h]acridine (10.0 g, 23.0 mmol), phenylacetylene (4.70 g, 46.0 mmol, 2.0 eq.), and bis (triphenylphosphine)-palladium chloride (3.23 g, 4.6 mmol, 0.2 eq.) were introduced, followed by a 1M-solution of tetrabutylammonium fluoride in THF (70 mL). The resulting mixture was warmed up to reflux and reacted for 2 h. After completion of the reaction, MeOH (70 mL) was added, and the solution was left to cool down to room temperature. The precipitate formed upon cooling was collected by filtration, washed with MeOH (2×50 mL), then hexane (3×50 mL), and finally dried under vacuum at 40° C.

Yield: about 7.0 g (about 67%, yellowish solid).

Step 2: Synthesis of 7-(3',4',5',6'-tetraphenyl-[1,1':2',1''-terphenyl]-4-yl)dibenzo[c,h]acridine

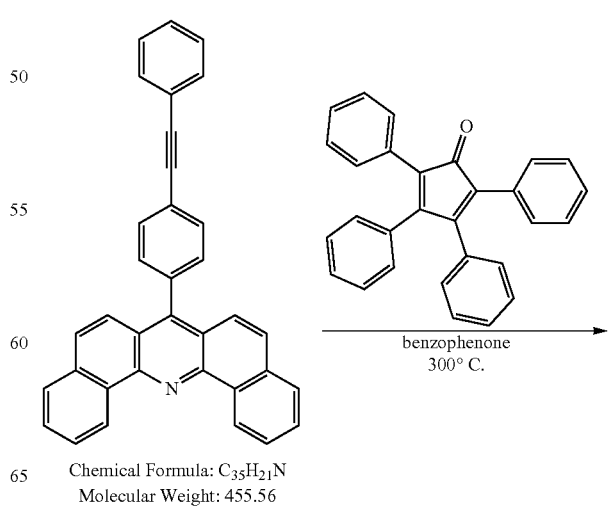

Chemical Formula: $C_{35}H_{21}N$
Molecular Weight: 455.56

-continued

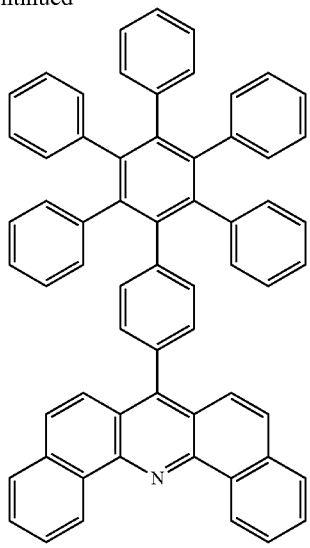

Chemical Formula: C$_{63}$H$_{41}$N
Molecular Weight: 812.03

A three necked 100-mL round bottom flask was charged with 7-(4-(phenylethynyl)phenyl)dibenzo[c,h]acridine (6.8 g, 14.9 mmol), 2,3,4,5-tetraphenylcyclopenta-2,4-dienone (6.31 g, 16.4 mmol, 1.1 eq.), and benzophenone (35 g as molten solvent). After degassing the solids with N$_2$, the resulting mixture was warmed up to 300° C. After 1 h of reflux at 300° C., gas evolution had stopped and the mixture was hence cooled down to ca. 80° C. Toluene (100 mL), was added, and the resulting precipitate was filtered off and washed with toluene (2×40 mL), followed by hexane (2×40 mL). The solid was then purified by trituration in hot chlorobenzene (60 mL), followed by trituration in hot MeOH (60 mL). After filtration and drying under vacuum at 120° C., the desired was isolated as a yellowish powder. Yield: about 6.8 g (about 56%, yellowish solid).

In Table 1 are summarized compounds of formula I and their starting material, yield, m/z, glass transition temperature, reduction potential against Fc/F$^+$ in tetrahydrofuran and dipole moment.

General Procedure for Fabrication of OLEDs

For top emission devices, Examples 1 to 16 and comparative examples 1 to 3, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode. 100 nm Ag were deposited as anode at a pressure of 10$^{-5}$ to 10$^{-7}$ mbar.

Then, 92 wt.-% Biphenyl-4-yl(9,9-diphenyl-9H-fluoren-2-yl)-[4-(9-phenyl-9H-carbazol-3-yl)phenyl]-amine (CAS 1242056-42-3) with 8 wt.-% of 2,2',2"-(cyclopropane-1,2,3-triylidene)tris(2-(p-cyanotetrafluorophenyl)acetonitrile) was vacuum deposited on the ITO electrode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 122 nm.

Then N,N-bis(4-(dibenzo[b,d]furan-4-yl)phenyl)-[1,1':4',1"-terphenyl]-4-amine (CAS 1198399-61-9) was vacuum deposited on the HTL, to form an electron blocking layer (EBL) having a thickness of 5 nm.

Then 97 wt.-% 2-(10-phenyl-9-anthracenyl)-benzo[b]naphtho[2,3-d]furan (CAS 1627916-48-6) as EML host and 3 wt.-% blue dopant were deposited on the EBL, to form a blue-emitting EML with a thickness of 20 nm. For Examples 1 to 16 and Comparative examples 1 to 3, NUBD370 (Sun Fine Chemicals) was used as fluorescent blue dopant.

Then the electron transport auxiliary layer 135, if present, is formed with a thickness of 5 nm by depositing 2,4-diphenyl-6-(4',5',6'-triphenyl-[1,1':2',1":3",1'":3'",1""-quinquephenyl]-3""-yl)-1,3,5-triazine on the emission layer according to Example 9 to 14 comparative example 2 (Table 2), or by depositing compound of formula I on the emission layer according to Example 15 and 16 and comparative example 3 (Table 4).

Then, the electron transport layer 34 is formed either directly on the emission layer according to Examples 1 to 8 and comparative example 1 (Table 2), or on the electron transport auxiliary layer according to Examples 9 to 16 and comparative examples 2 and 3. If the electron transport layer is in direct contact with the emission layer, the thickness is 36 nm. If the electron transport layer is deposited on top of the electron transport auxiliary layer, the thickness is 31 nm. The electron transport layer comprises 50 wt.-% matrix compound and 50 wt.-% of LiQ. The composition is shown in Table 2, 3 and 4.

Then the electron injection layer 36 is formed on the electron transport layer 34 by deposing LiQ with a thickness of 1.5 nm or Yb with a thickness of 2 nm, see Tables 2, 3 and 4.

The cathode was evaporated at ultra-high vacuum of 10$^{-7}$ mbar. Therefore, a thermal single co-evaporation of one or several metals was performed with a rate of 0, 1 to 10 nm/s (0.01 to 1 Å/s) in order to generate a homogeneous cathode with a thickness of 5 to 1000 nm. The cathode was formed from 13 nm magnesium silver alloy (90:10 vol.-%) or from 11 nm Ag, see Tables 2, 3 and 4.

A cap layer of Biphenyl-4-yl(9,9-diphenyl-9H-fluoren-2-yl)-[4-(9-phenyl-9H-carbazol-3-yl)phenyl]-amine was formed on the cathode with a thickness of 60 nm in case of MgAg cathode and 75 nm in case of Ag cathode.

The OLED stack is protected from ambient conditions by encapsulation of the device with a glass slide. Thereby, a cavity is formed, which includes a getter material for further protection. To assess the performance of the inventive examples compared to the prior art, the current efficiency is measured under ambient conditions (20° C.). Current voltage measurements are performed using a Keithley 2400 sourcemeter, and recorded in V. At 10 mA/cm$^2$ for top emission devices, a calibrated spectrometer CAS140 from Instrument Systems is used for measurement of CIE coordinates and brightness in Candela. Lifetime LT of the device is measured at ambient conditions (20° C.) and 10 mA/cm$^2$, using a Keithley 2400 sourcemeter, and recorded in hours.

The brightness of the device is measured using a calibrated photo diode. The lifetime LT is defined as the time till the brightness of the device is reduced to 97% of its initial value.

The light output in external efficiency EQE and power efficiency (lm/W efficiency) are dertermined at 10 mA/cm$^2$ for top emission devices.

To determine the efficiency EQE in % the light output of the device is measured using a calibrated photodiode.

To determine the power efficiency in lm/W, in a first step the luminance in candela per square meter (cd/m2) is measured with an array spectrometer CAS140 CT from Instrument Systems which has been calibrated by Deutsche Akkreditierungsstelle (DAkkS). In a second step, the luminance is then multiplied by π and divided by the voltage and current density.

In bottom emission devices, the emission is predominately Lambertian and quantified in percent external quantum efficiency (EQE) and power efficiency in lm/W.

In top emission devices, the emission is forward directed, non-Lambertian and also highly dependent on the microcavity. Therefore, the external quantum efficiency (EQE) and power efficiency in lm/W will be higher compared to bottom emission devices.

Technical Effect of the Invention

Top Emission Devices

Referring to Table 2, the organic light emitting diodes according to Examples 1 to 8 exhibited improved luminance efficiency and/or life-span characteristics simultaneously compared with the organic light emitting diode according to Comparative Example 1.

In comparative example 1, the electron transport layer comprises acridine compound MX1 and alkali organic complex LiQ. The formula of MX1 is

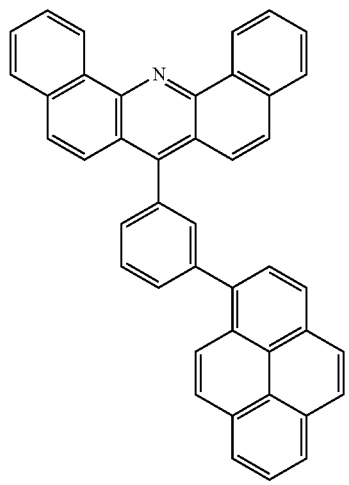

The glass transition temperature is 128° C., the reduction potential is −2.26 V against Fc/Fc$^+$ in tetrahydrofuran and the dipole moment is −1.8 Debye. The operating voltage is 3.4 V, the efficiency is 7.2 cd/A and the lifetime is 46 hours.

In examples 1, 2 and 3, the electron transport layer comprises a compound of formula I with a+b+c+d+e=2 and alkali organic complex LiQ. The operating voltage is between 3.47 and 3.57 V, the efficiency is significantly improved to 7.8 to 8.5 cd/A and the lifetime is significantly improved to 55 to 62 hours.

In example 4, 5 and 6, the electron transport layer comprises the same compound of formula I with a+b+c+d+e=2, the electron injection layer comprises 2 nm Yb and the cathode comprises Ag. The operating voltage is between to 3.31 and 3.56 V. The efficiency is further increased to 8.3 to 8.8 cd/A.

In example 7 and 8, the electron transport layer comprises the same compound of formula I with a+b+c+d+e=4, the electron injection layer comprises 2 nm Yb and the cathode comprises Ag. The operating voltage is between to 3.56 and 3.71 V. The efficiency is further increased to 9.2 cd/A. In particular for compound ETM-16, the lifetime is dramatically improved to 91 hours.

In summary, much improved cd/A efficiency is obtained when a compound of formula I is used in the electron transport layer. Particularly good performance is obtained for compounds of formula I wherein a+b+c+d+e=4.

Referring to Table 3, the organic light emitting diodes according to Examples 9 to 14 exhibited improved luminance efficiency and/or life-span characteristics simultaneously compared with the organic light emitting diode according to Comparative Example 2.

In comparative example 2, the electron transport auxiliary layer (a-ETL) 135 comprises 2,4-diphenyl-6-(4',5',6'-triphenyl-[1,1':2',1'':3'',1''':3''',1''''-quinquephenyl]-3''''-yl)-1,3,5-triazine. The electron transport layer (ETL) 34 comprises acridine compound MX2 and alkali organic complex LiQ. The formula of MX2 is

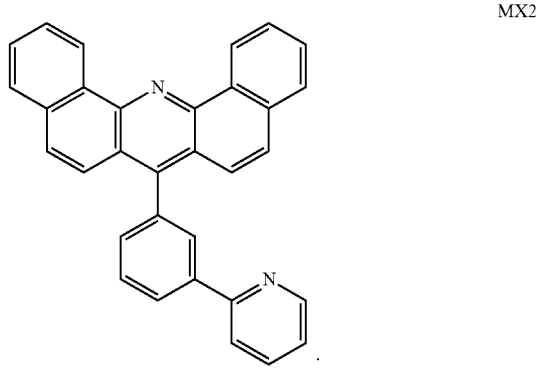 [SMILES: c1ccc(-c2cccc(-c3c4ccc5ccccc5c4nc4c3ccc3ccccc34)c2)nc1]

The glass transition temperature is 92° C., the reduction potential is −2.29 V against Fc/Fc$^+$ in tetrahydrofuran. The operating voltage is 3.41 V, the efficiency is 6.5 cd/A and the lifetime is 33 hours.

In examples 9 to 12, the electron transport layer comprises a compound of formula I wherein a+b+c+d+e=2 and alkali organic complex LiQ. The operating voltage is between 3.33 and 3.56 V, the efficiency is significantly improved to 8.1 to 8.9 cd/A. In example 9 and 11, the lifetime is improved to 44 and 45.5 hours, respectively.

In examples 13 and 14, the electron transport layer comprises a compound of formula I wherein a+b+c+d+e=4 and alkali organic complex LiQ. The operating voltage is between 3.77 and 3.78 V, the efficiency is further improved to 9.1 and 9.2 cd/A, respectively.

Referring to Table 4, the organic light emitting diodes according to Examples 15 and 16 exhibited improved luminance efficiency and/or life-span characteristics simultaneously compared with the organic light emitting diode according to Comparative Example 3.

In comparative example 3, the electron transport auxiliary layer (a-ETL) 135 comprises acridine compound MX2. The electron transport layer (ETL) 34 comprises 2-([1,1'-biphenyl]-4-yl)-4-(9,9-diphenyl-9H-fluoren-4-yl)-6-phenyl-1,3,5-triazine (MX4, CAS 1801992-44-8) and alkali organic complex LiQ. The electron injection layer (EIL) 36 comprises LiQ. The operating voltage is 3.34 V, the efficiency is 6.8 cd/A and the lifetime is 60 hours.

In example 15, the a-ETL comprises a compound of formula I wherein a+b+c+d+e=2. The operating voltage is 3.33 V, the efficiency is significantly improved to 8.5 cd/A. The lifetime is 39 hours.

In example 16, the a-ETL comprises a compound of formula I wherein a+b+c+d+e=4. The operating voltage is 3.42 V, the efficiency is significantly improved to 9.2 cd/A. The lifetime is 21.5 hours.

In summary, much improved cd/A efficiency is obtained when a compound of formula I is used in the electron transport layer. Particularly good performance is obtained for compounds of formula I wherein a+b+c+d+e=4.

TABLE 1
Compounds of formula (I)
| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-1 | 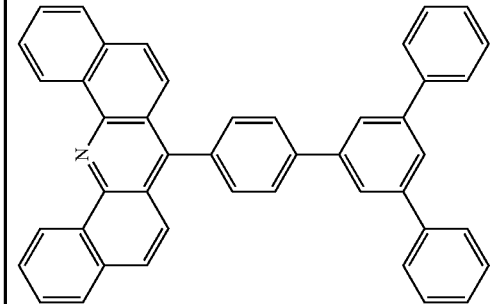 | 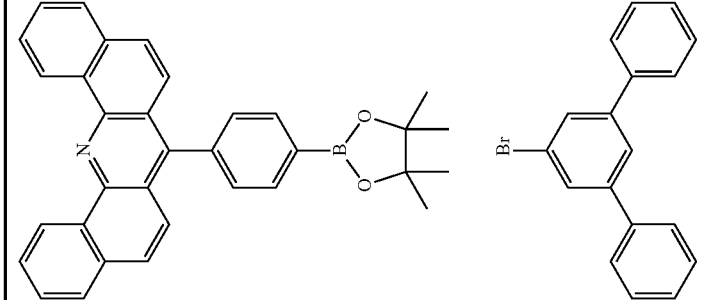 | 83% | — | 130 | −2.25 | — |

TABLE 1-continued
Compounds of formula (I)
| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-2 | 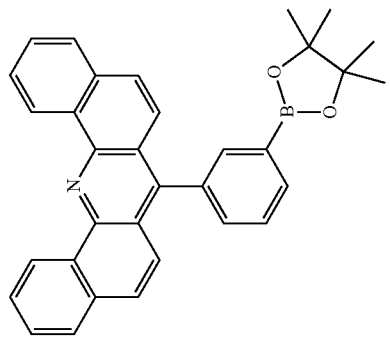 | 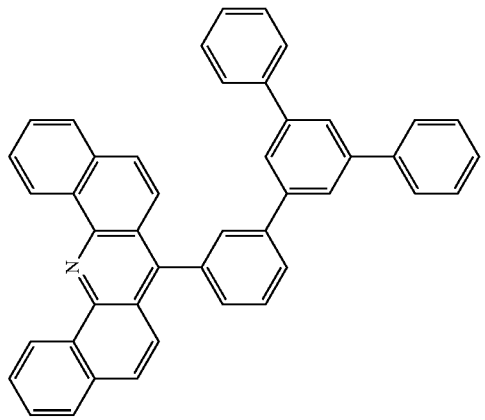 | 68% | — | 122 | −2.27 | 1.87 |

TABLE 1-continued

Compounds of formula (I)

| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-3 | | | 68% | 660 | 127 | −2.26 | — |

TABLE 1-continued
Compounds of formula (I)
| Referred to as: | Starting materials | Compound of formula I | Yield [%] | m/z | Tg [°C.] | Reduction potiential against Fc/Fc+ [V] | Dipole moment [Debye] |
|---|---|---|---|---|---|---|---|
| ETM-4 | 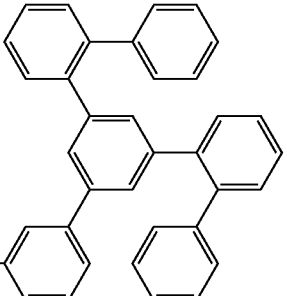 | 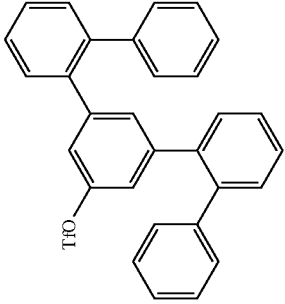 | 51% | — | 130 | — | — |

TABLE 1-continued
Compounds of formula (I)
| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-5 | 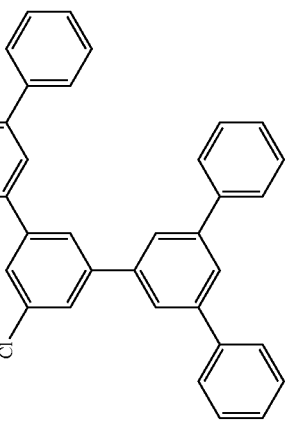 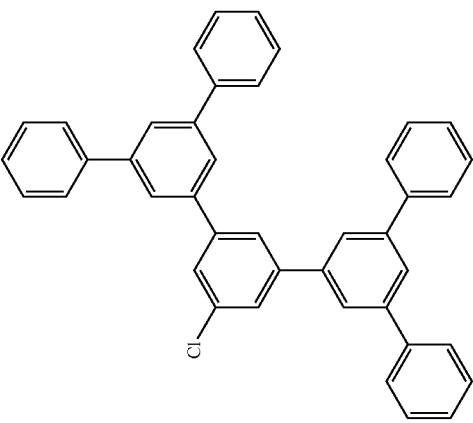 | 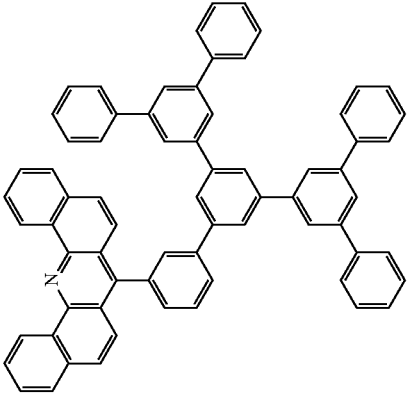 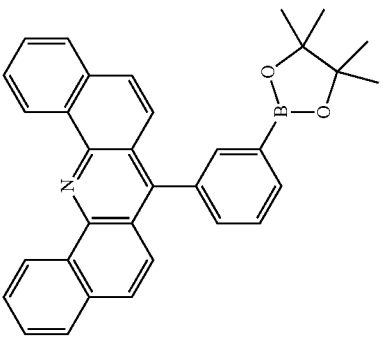 | 18% | — | 162 | — | — |

TABLE 1-continued
Compounds of formula (I)
| Referred to as: | Starting materials | Compound of formula I | Yield [%] | m/z | Tg [°C.] | Reduction potiential against Fc/Fe+ [V] | Dipole moment [Debye] |
|---|---|---|---|---|---|---|---|
| ETM-6 | 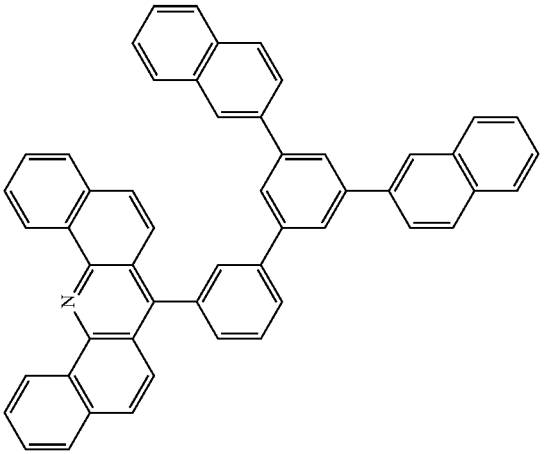 | 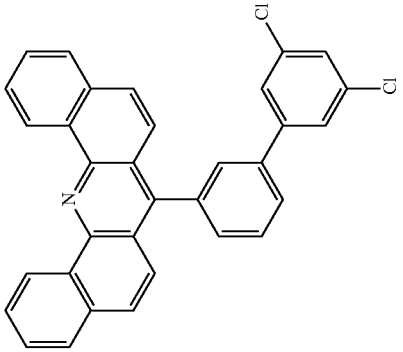 | 38% | — | 136 | −2.27 | — |

TABLE 1-continued
Compounds of formula (I)
| Referred to as: | Starting materials | Compound of formula I | Yield [%] | m/z | Tg [°C.] | Reduction potential against Fc/Fe+ [V] | Dipole moment [Debye] |
|---|---|---|---|---|---|---|---|
| ETM-7 | 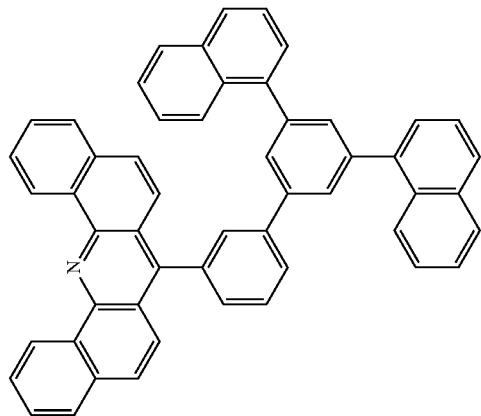 | 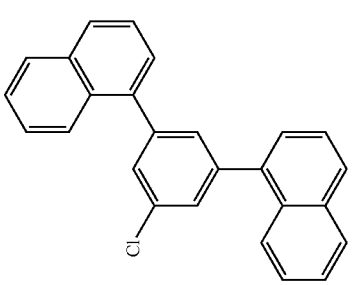 | 20% | — | 148 | — | — |

TABLE 1-continued
| Referred to as: | Compounds of formula (I) | | | | | |
|---|---|---|---|---|---|---|
| | Starting materials | Compound of formula I | Yield [%] | m/z | Tg [°C.] | Reduction potential against Fc/Fc+ [V] | Dipole moment [Debye] |
| ETM-8 | 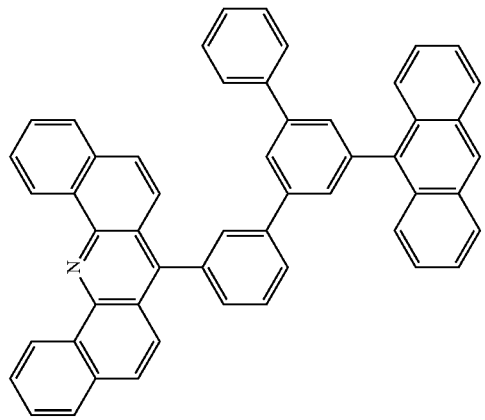 | 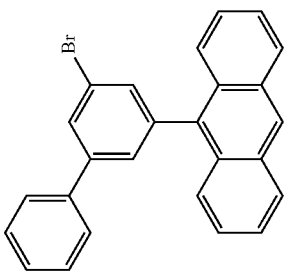 | 80% | — | 167 | −2.30 | — |

TABLE 1-continued
| Referred to as: | Starting materials | Compound of formula I | Yield [%] | m/z | Tg [°C.] | Reduction potiential against Fc/Fe+ [V] | Dipole moment [Debye] |
|---|---|---|---|---|---|---|---|
| ETM-9 | 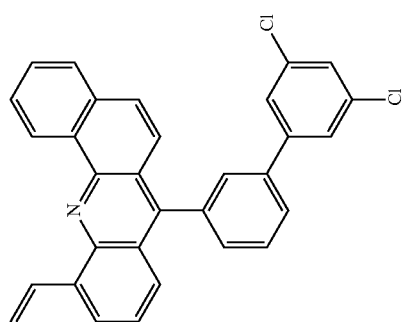 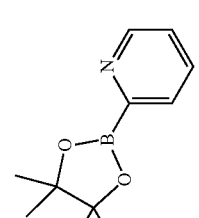 | 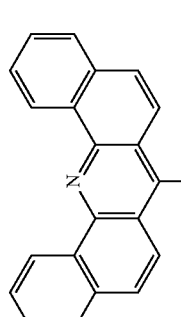 | 88% | — | 134 | −2.26 | 0.98 |

TABLE 1-continued

Compounds of formula (I)

| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-10 | | | 75% | 660 | 125 | −2.28 | 1.70 |

TABLE 1-continued

Compounds of formula (I)

| Referred to as: | Starting materials | Compound of formula I | Yield [%] | m/z | Tg [°C.] | Reduction potential against Fc/Fe+ [V] | Dipole moment [Debye] |
|---|---|---|---|---|---|---|---|
| ETM-11 | | | 49% | 736 | 151 | −2.28 | 1.88 |

TABLE 1-continued
Compounds of formula (I)
| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-12 | 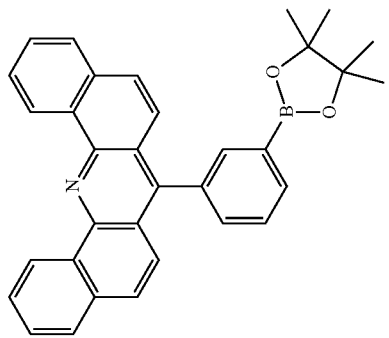 | 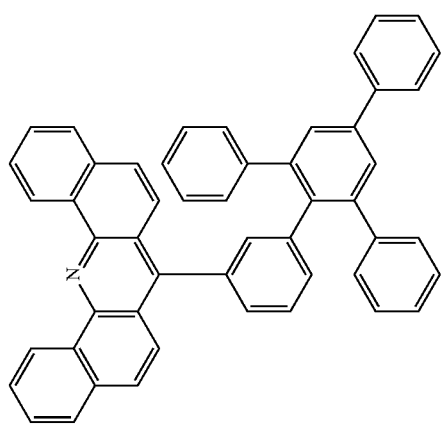 | 25% | — | 130 | −2.31 | — |

TABLE 1-continued

Compounds of formula (I)

| Referred to as: | Starting materials | Compound of formula I | Yield [%] | m/z | Tg [°C.] | Reduction potiential against Fc/Fe+ [V] | Dipole moment [Debye] |
|---|---|---|---|---|---|---|---|
| ETM-13 | | | 58% | — | 159 | −2.29 | 2.15 |

TABLE 1-continued

| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-14 | | | 62% | — | 175 | −2.25 | — |

TABLE 1-continued

Compounds of formula (I)

| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-15 | | | 50% | — | 175 | — | — |

TABLE 1-continued
Compounds of formula (I)
| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-16 | 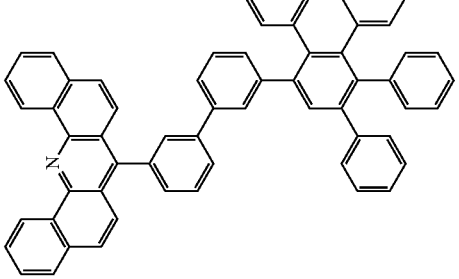 | 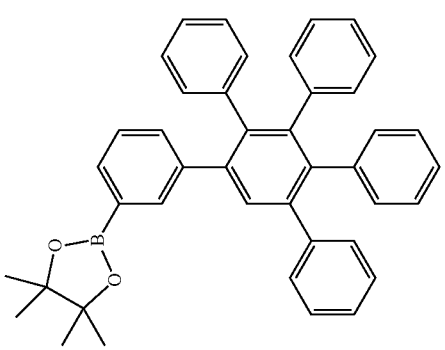 | 86% | 812 | 165 | −2.29 | 2.62 |

TABLE 1-continued
Compounds of formula (I)
| Referred to as: | Starting materials | Compound of formula I | Yield [%] | m/z | Tg [°C.] | Reduction potential against Fc/Fc+ [V] | Dipole moment [Debye] |
|---|---|---|---|---|---|---|---|
| ETM-17 | 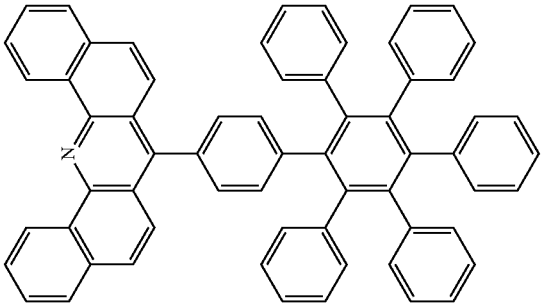 | 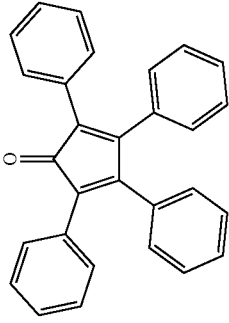 | 55% | — | not observed | −2.31 | — |

TABLE 2

Performance at 10 mA/cm² of top emission devices comprising an ETL (34) comprising a compound of formula I and a lithium organic complex and an EIL (36)

| | ETL | EIL | Cathode | Voltage (V) [10 mA/cm²] | Efficiency (cd/A) [10 mA/cm²] | LT97 (h) |
|---|---|---|---|---|---|---|
| Comparative example 1 | MX1:LiQ | LiQ | Mg:Ag | 3.39 | 7.2 | 46 |
| Example 1 | ETM-2:LiQ | LiQ | Mg:Ag | 3.56 | 8.5 | 62 |
| Example 2 | ETM-8:LiQ | LiQ | Mg:Ag | 3.47 | 7.8 | 60 |
| Example 3 | ETM-9:LiQ | LiQ | Mg:Ag | 3.57 | 7.9 | 55 |
| Example 4 | ETM-1:LiQ | Yb | Ag | 3.31 | 8.8 | 25 |
| Example 5 | ETM-3:LiQ | Yb | Ag | 3.50 | 8.3 | 81 |
| Example 6 | ETM-6:LiQ | Yb | Ag | 3.56 | 8.7 | 29 |
| Example 7 | ETM-13:LiQ | Yb | Ag | 3.71 | 9.2 | 10 |
| Example 8 | ETM-16:LiQ | Yb | Ag | 3.56 | 9.2 | 91 |

TABLE 3

Performance at 10 mA/cm² of top emission devices comprising an a-ETL (135), an ETL (34) comprising a compound of formula I and a lithium organic complex and an EIL (36)

| | a-ETL | ETL | EIL | Cathode | Voltage (V) | Efficiency (cd/A) | LT97 (h) |
|---|---|---|---|---|---|---|---|
| Comparative example 2 | MX3 | MX2:LiQ | LiQ | Mg:Ag | 3.41 | 6.5 | 33 |
| Example 9 | MX3 | ETM-9:LiQ | LiQ | Mg:Ag | 3.44 | 8.1 | 44 |
| Example 10 | MX3 | ETM-1:LiQ | Yb | Ag | 3.33 | 8.7 | 22 |
| Example 11 | MX3 | ETM-3:LiQ | Yb | Ag | 3.54 | 8.9 | 45.5 |
| Example 12 | MX3 | ETM-6:LiQ | Yb | Ag | 3.56 | 8.7 | 19 |
| Example 13 | MX3 | ETM-13:LiQ | Yb | Ag | 3.78 | 9.1 | 13.5 |
| Example 14 | MX3 | ETM-17:LiQ | Yb | Ag | 3.77 | 9.2 | 5 |

TABLE 4

Performance at 10 mA/cm² of top emission devices comprising an a-ETL (135) comprising a compound of formula I, an ETL (34) comprising a matrix compound and a lithium organic complex and an EIL (36)

| | a-ETL | ETL | EIL | Cathode | Voltage (V) | Efficiency (cd/A) | LT97 (h) |
|---|---|---|---|---|---|---|---|
| Comparative example 3 | MX2 | MX4:LiQ | LiQ | Mg:Ag | 3.34 | 6.8 | 60 |
| Example 15 | ETM-2 | MX4:LiQ | LiQ | Mg:Ag | 3.33 | 8.5 | 39 |
| Example 16 | ETM-13 | MX4:LiQ | Yb | Ag | 3.42 | 9.2 | 21.5 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound of formula (I)

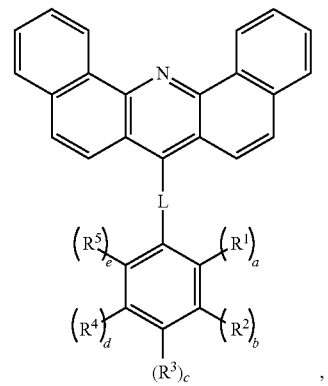

wherein

L is selected from phenylene, naphthylene and biphenylene;

$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy;

a, b, c, d and e are independently selected from 0 or 1 and $2 \leq a+b+c+d+e \leq 5$.

2. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy;
a, b, c, d and e are independently selected from 0 or 1 and $3 \leq a+b+c+d+e \leq 5$.

3. The compound according to claim 2, wherein $4 \leq a+b+c+d+e \leq 5$.

4. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, c and e are each selected 0, and b and d are each selected 1.

5. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy;
c and e are each selected 0, and a, b and d are each selected 1.

6. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
e is each selected 0, and a, b, c and d are each selected 1.

7. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a and c are each selected 1, and b, d and e are each selected 0.

8. The compound of formula (I) according to claim 1, wherein
L is selected from phenylene, naphthylene and biphenylene; and
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, b and c are each selected 1, and d and e are each selected 0.

9. The compound of formula (I) according to claim 1, wherein
L is selected from phenylene, naphthylene and biphenylene; and
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, b, c and e are each selected 1, and d is selected 0.

10. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a and e are each selected 1, and b, d and c are each selected 0.

11. The compound of formula (I) according to claim 1, wherein
L is selected from phenylene, naphthylene and biphenylene;
$R^1$, $R^2$, $R^3$, $R^4$ and $R^5$ are independently selected from unsubstituted or substituted $C_6$ to $C_{18}$ aryl and unsubstituted or substituted pyridyl; and the substituents are selected from deuterium, $C_1$ to $C_{12}$ alkyl and $C_1$ to $C_{12}$ alkoxy; and
a, c and e are each selected 1, and b and d are each selected 0.

12. The compound of formula (I) according to claim 1, wherein
$R^1$, $R^2$, $R^3$, $R^4$ and $R^5$ are independently selected from unsubstituted or substituted $C_6$ to $C_{18}$ aryl.

13. The compound of formula (I) according to claims 1, selected from the formula (D1) to (D25):

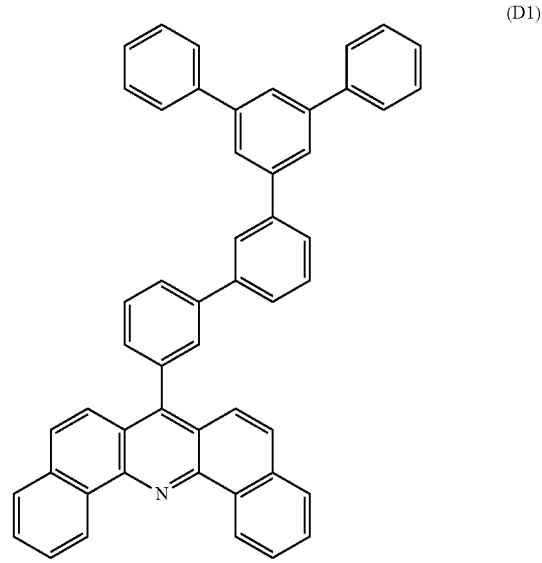

(D1)

(D2)
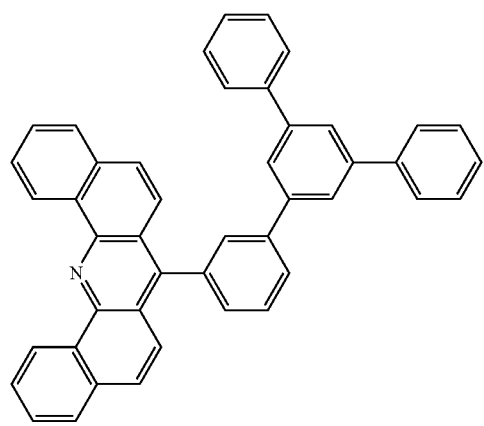
(D3)
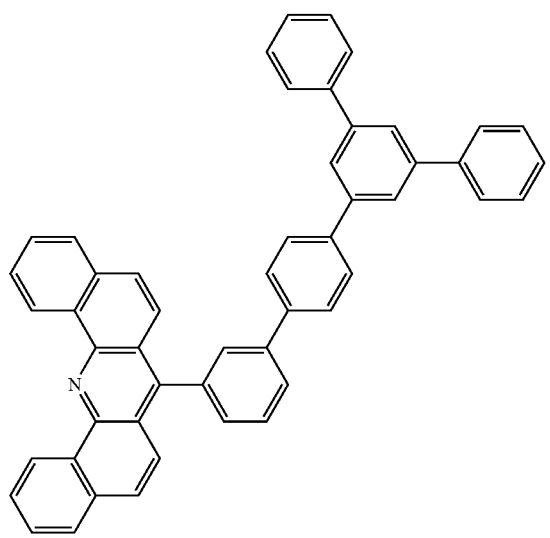
(D4)
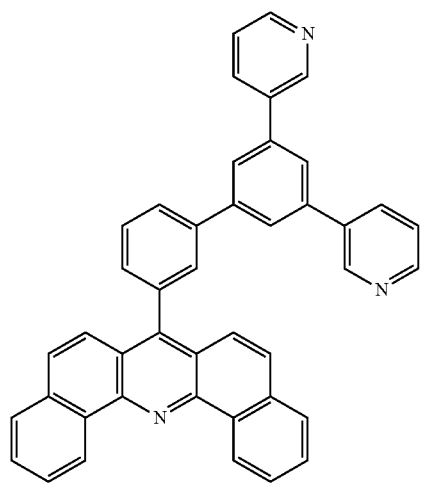
(D5)
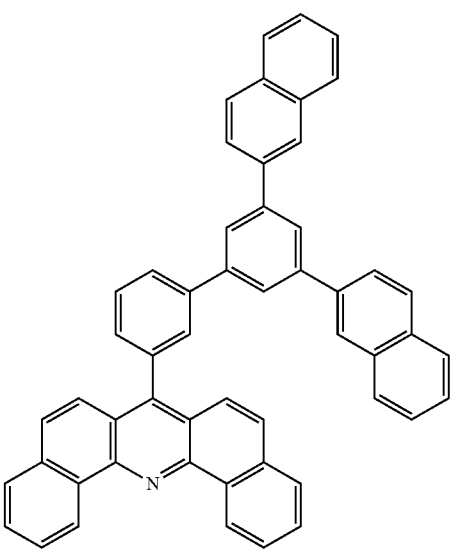
(D6)
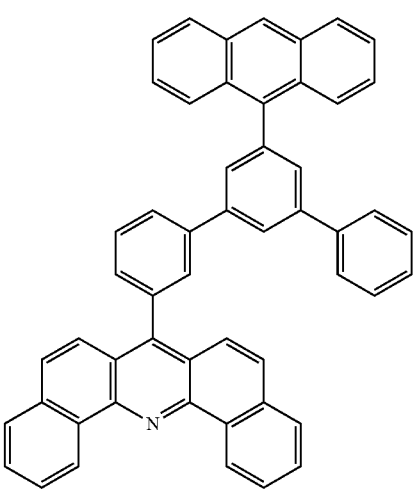
(D7)
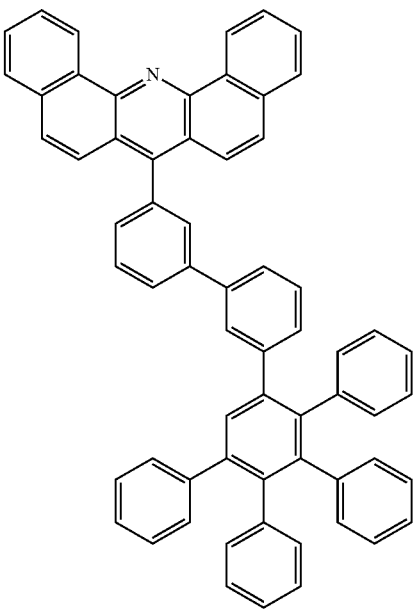

(D8)
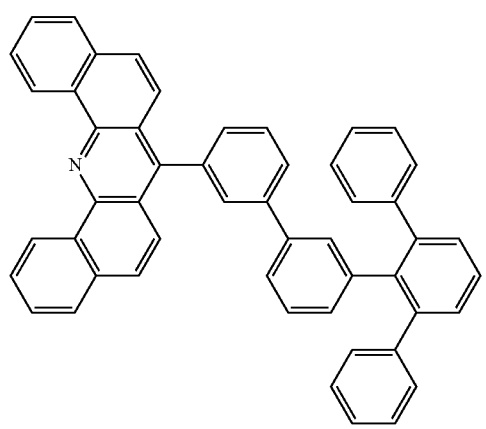
(D9)
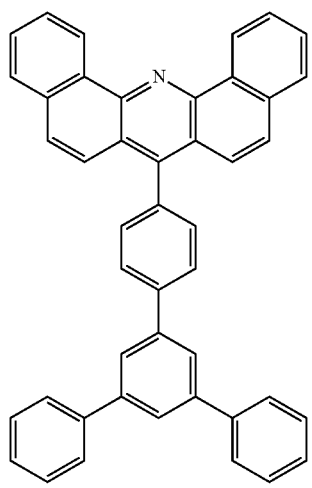 [SMILES: c1ccc(-c2cc(-c3ccccc3)cc(-c3ccc(-c4c5ccc6ccccc6c5nc5c4ccc4ccccc45)cc3)c2)cc1]
(D10)
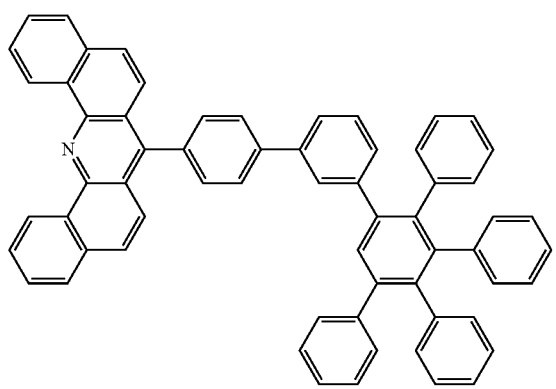
(D11)
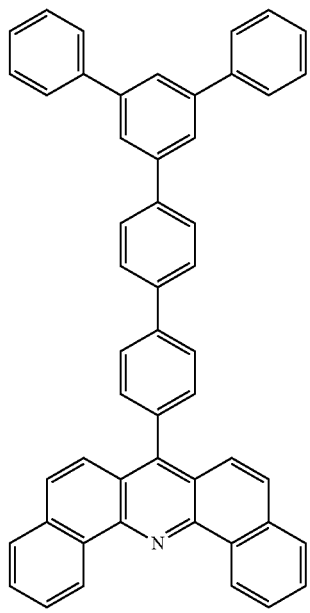
(D12)
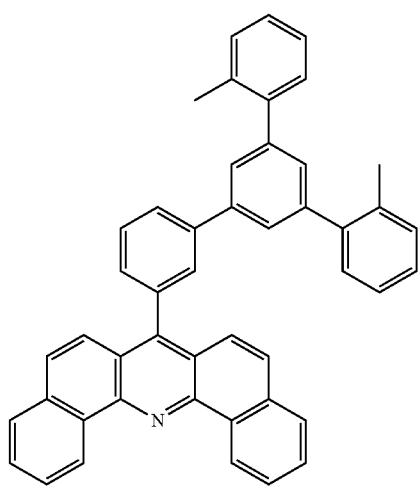
(D13)
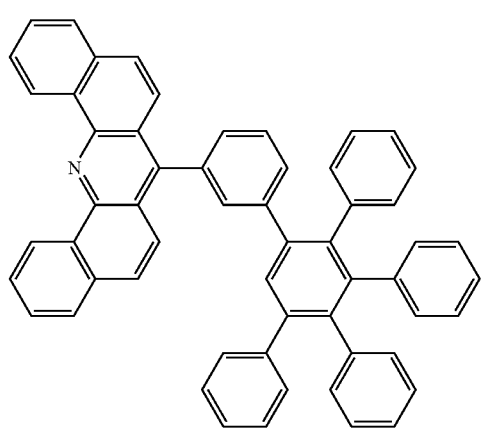

(D14)
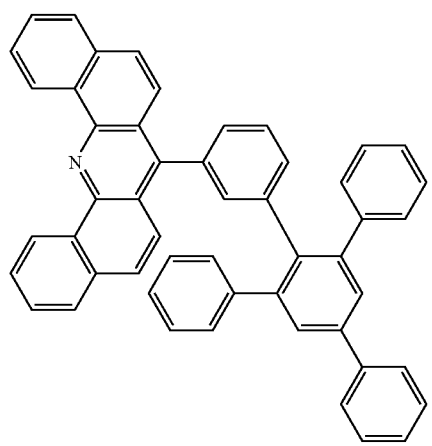
(D15)
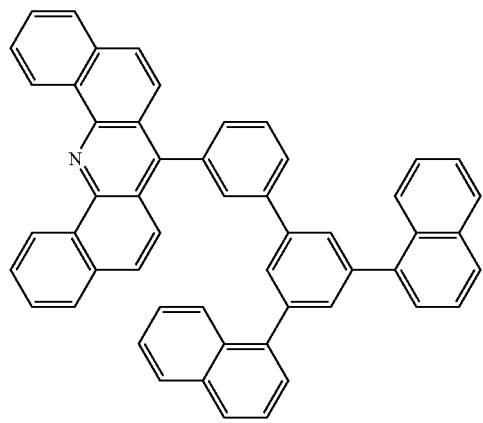
(D16)
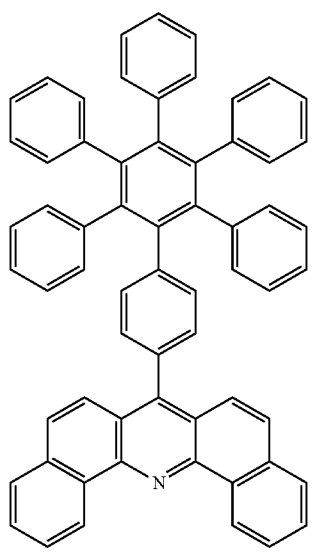
(D17)
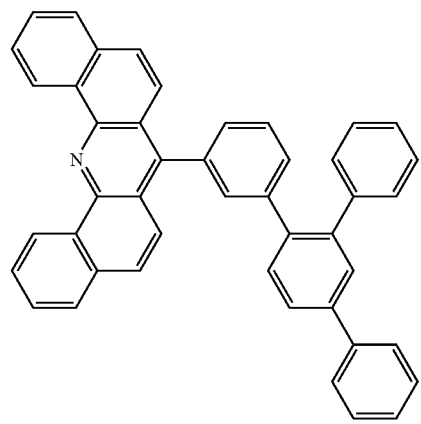
(D18)
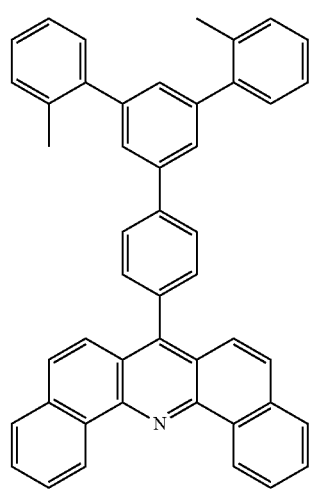
(D19)
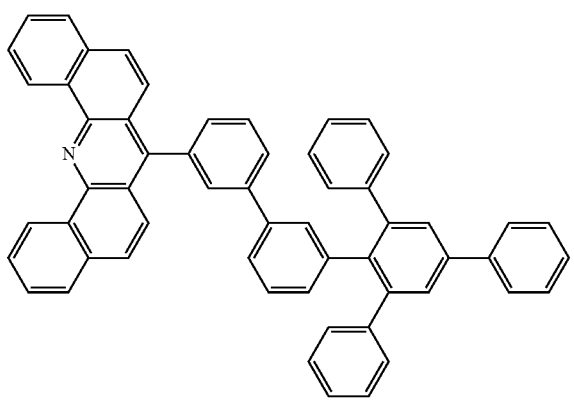
(D20)
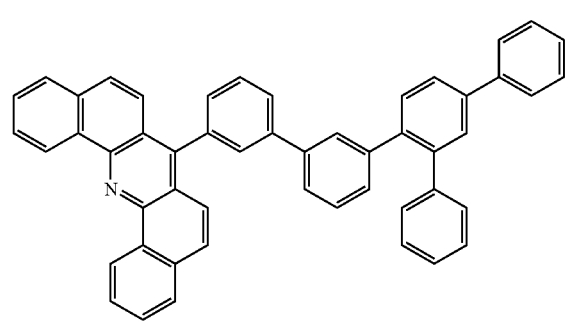

(D21)
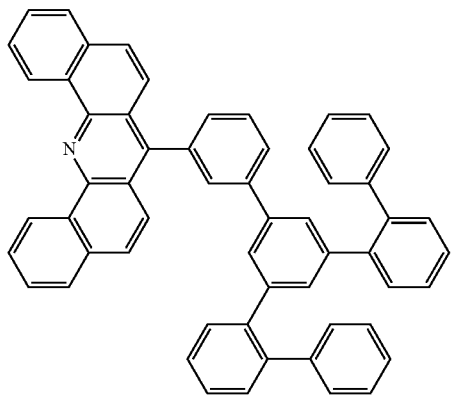

(D22)
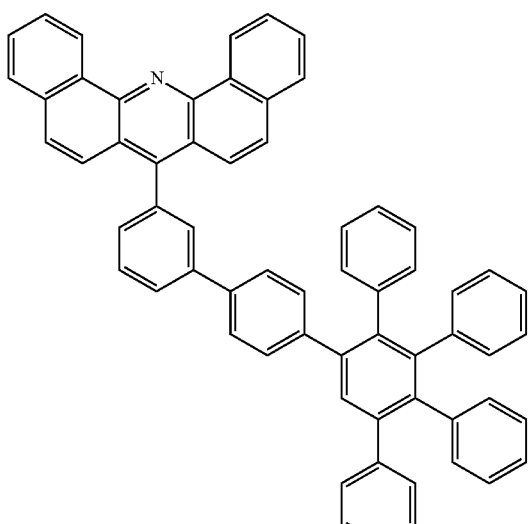

(D23)
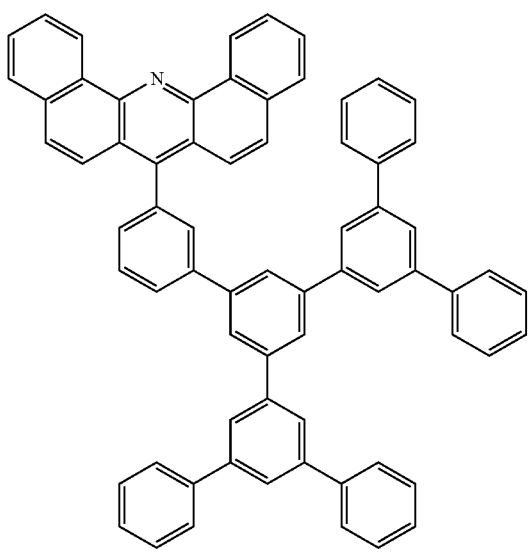 [SMILES: c1ccc(-c2cc(-c3ccccc3)cc(-c3cc(-c4cc(-c5ccccc5)cc(-c5ccccc5)c4)cc(-c4cccc(-c5c6ccc7ccccc7c6nc6c5ccc5ccccc56)c4)c3)c2)cc1]

(D24)
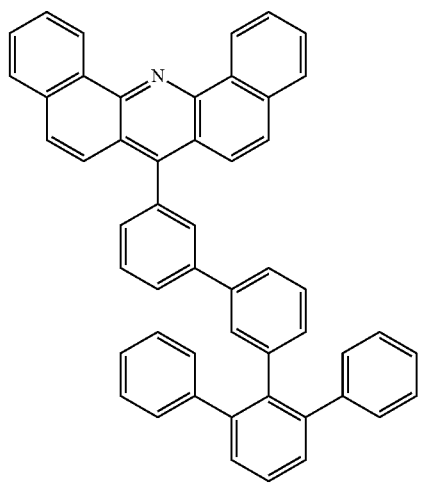

(D25)
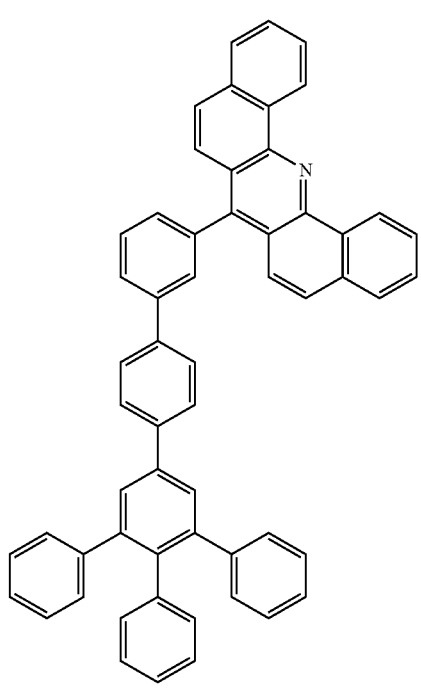

14. An organic semiconductor material comprising a compound of formula (I) according to claim 1.

15. The organic semiconductor material according to claim 14, wherein the organic semiconductor material further comprises an alkali halide or alkali organic complex.

16. An organic semiconductor layer comprising a compound of formula (I) according to claim 1.

17. The organic semiconductor layer according to claim 16, wherein the organic semiconductor layer further comprises an alkali halide and/or alkali organic complex.

18. An electronic device comprising a compound of formula (I) according to claim 1.

19. The electronic device according to claim 18, wherein the electronic device is an organic electroluminescent device.

20. The electronic device according to claim 19, wherein the electronic device comprises an organic semiconductor layer according to claims 15.

* * * * *